United States Patent
Soto-Gutierrez et al.

(10) Patent No.: US 11,866,733 B2
(45) Date of Patent: Jan. 9, 2024

(54) HUMAN INDUCED PLURIPOTENT STEM CELLS FOR HIGH EFFICIENCY GENETIC ENGINEERING

(71) Applicant: University of Pittsburgh—Of the Commonwealth System of Higher Education, Pittsburgh, PA (US)

(72) Inventors: Alejandro Soto-Gutierrez, Pittsburgh, PA (US); Alexandra Sylvie Collin de l'Hortet, Pittsburgh, PA (US); Kan Handa, Pittsburgh, PA (US); Jorge Guzman Lepe, Pittsburgh, PA (US); Yang Wang, Pittsburgh, PA (US); Kazuki Takeishi, Pittsburgh, PA (US); Ira Jacob Fox, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/322,087

(22) PCT Filed: Jul. 31, 2017

(86) PCT No.: PCT/US2017/044719
§ 371 (c)(1),
(2) Date: Jan. 30, 2019

(87) PCT Pub. No.: WO2018/026723
PCT Pub. Date: Feb. 8, 2018

(65) Prior Publication Data
US 2019/0185819 A1 Jun. 20, 2019

Related U.S. Application Data

(60) Provisional application No. 62/369,698, filed on Aug. 1, 2016.

(51) Int. Cl.
*C12N 5/074* (2010.01)
*C12N 15/11* (2006.01)
*C12N 9/22* (2006.01)

(52) U.S. Cl.
CPC ............ *C12N 5/0696* (2013.01); *C12N 9/22* (2013.01); *C12N 15/11* (2013.01); *C12N 15/111* (2013.01); *C12N 2310/20* (2017.05); *C12N 2320/12* (2013.01); *C12N 2330/51* (2013.01); *C12N 2501/602* (2013.01); *C12N 2501/603* (2013.01); *C12N 2501/604* (2013.01); *C12N 2501/608* (2013.01); *C12N 2506/1307* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2014/0155468 A1* | 6/2014 | Gregory | A61P 13/12 514/44 R |
| 2015/0191744 A1* | 7/2015 | Wolfe | C12Q 1/6841 435/6.11 |
| 2018/0141992 A1* | 5/2018 | Cowan | C07K 14/70539 |

FOREIGN PATENT DOCUMENTS

| WO | WO 2016/012544 | 1/2016 | |
|---|---|---|---|
| WO | WO-2016012544 A2 * | 1/2016 | ........... C12N 15/113 |

OTHER PUBLICATIONS

Gonzalez et al Cell Stem Cell.; 15(2): 215-226 (Year: 2014).*
Oliveri et al. Regenerative Medicine, 2(5): 795-816 (Year: 2007).*
Sullivan et al. Reproductive BioMed. Online, 16(1): 41-50 (Year: 2008).*
Djuric and Ellis, Stem Cell Research and Therapy, 2010, 1:3 (Year: 2010).*
Cyranoski, Nature, 516: 162-164 (Year: 2014).*
Aasen et al., Nature Biotechnology, 26(11): 1276-1284 (Year: 2008).*
Kojima and Ieda, Cell. Mol. Life Sci., 74, 2203-2215 (Year: 2017).*
Lalit et al.,Cell Stem Cell 18, 354-36 (Year: 2016).*
Balboa et al Stem cell reports, 5(3), 448-459 (Year: 2015).*
Hsu et al Nat Biotechnology. Sep;31(9):827-32 (Year: 2013).*
Dow et al Trends in Molecular Medicine, , 21, 609-621 (Year: 2015).*
Kosicki et al Nature Biotechnology, 1-8 (Year: 2018).*
Brouwer et al Stem Cell Rev and Rep 12:54-72 (Year: 2016).*
Lohle et al Stem cells, 30, 570-579 (Year: 2012).*
Gonzalez et al Cell Stem Cell 15, 215-226, (Year: 2014).*
Senis et al Biotechnology. J. 9, 1402-1412). (Year: 2014).*
Gonzalez et al Cell Stem Cell. Aug. 7; 15(2): 215-226, (Year: 2014).*
Balboa et al., "Conditionally stabilized dCas9 activator for controlling gene expression in human cell reprogramming and differentiation," Stem Cell Reports, 5(3), 448-459 (Sep. 8, 2015).

(Continued)

*Primary Examiner* — Anoop K Singh
(74) *Attorney, Agent, or Firm* — Klarquist Sparkman, LLP

(57) ABSTRACT

Methods are disclosed herein for efficiently generating human induced pluripotent stem cells (iPSC) containing a nucleic acid including a doxycycline promoter operably linked to a nucleic acid encoding Cas9. These methods include transfecting a human somatic cell with a nucleic acid molecule comprising a doxycycline promoter operably linked to a nucleic acid encoding a Cas9, and constitutive promoter operably linked to a tetracycline responsive element and inducing the somatic cell to form an iPSC, thereby producing an iPSC that can undergo CRISPR/Cas9-mediated recombination at a high efficiency. The human iPSC, or a cell differentiated therefrom, is cultured in the presence of doxycycline to induce expression of the Cas9. These cells can then be used to target in any gene of interest by introducing nucleic acids encoding sgRNAs. Induced pluripotent stem cells produced by these methods are also disclosed.

12 Claims, 12 Drawing Sheets

Specification includes a Sequence Listing.

(56) References Cited

OTHER PUBLICATIONS

Bersten et al., "Inducible and reversible lentiviral and recombination mediated cassette exchange (RMCE) systems for controlling gene expression," *PLoS One* 10(3): e0116373, 20 pages, (Mar. 13, 2015).

Borkent et al., "A serial shRNA screen for roadblocks to reprogramming identifies the protein modifier SUMO2," *Stem Cell Reports* 6: 704-716 (May 10, 2016).

Gao et al., "Comparison of TALE designer transcription factors and the CRISPR/dCas9 in regulation of gene expression by targeting enhancers," *Nucleic Acids Research* 42(20): e155, 14 pages, (e-Pub Sep. 15, 2014).

Gomez-Martinez et al., "Generation of stable human cell lines with tetracycline-inducible (Tet-on) shRNA or cDNA expression," *Journal of Visualized Experiments* 73: e50171, 7 pages, (2013).

International Search Report from parent PCT Application No. PCT/US2017/044719, 5 pages (dated Sep. 17, 2017).

Klingenstein et al., "TBX3 knockdown decreases reprogramming efficiency of human cells," *Stem Cells International* 2016: 6759343, 7 pages, (e-Pub Nov. 30, 2015).

Written Opinion from parent PCT Application No. PCT/US2017/044719, 6 pages (dated Sep. 17, 2017).

Cao et al., "An easy and efficient inducible CRISPR/Cas9 platform with improved specificity for multiple gene targeting," *Nucleic Acids Research* 44(19): e149, 10 pages (e-PUB Jul. 25, 2016).

Castano et al., "Generation and characterization of a human iPSC cell line expressing inducible Cas9 in the "safe harbor" AAVS1 locus," *Stem Cell Research* 21: 137-140 (May 1, 2017).

Dow et al., "Inducible in vivo genome editing with CRISPR-Cas9," *Nature Biotechnology* 33(4): 390-394 (e-PUB Feb. 18, 2015).

Gonzalez et al., "An iCRISPR platform for rapid, multiplexable, and inducible genome editing in human pluripotent stem cells," *Cell Stem Cell* 15: 215-226 (Aug. 7, 2014).

Guo et al., "An inducible CRISPR-ON system for controllable gene activation in human pluripotent stem cells," *Protein Cell* 8(5): 379-393 (Jan. 23, 2017).

Greenberg, "Reprogramming to Pluripotency Using Small Molecule Compounds," Theses and Dissertations (ETD), University of Tennessee Health Science Center, UTHSC Digital Commons, Dec. 2015, available on-line at https://de.uthsc.edu/cgi/viewcontent.cgi?article=1103&context=dissertations.

Guo and Chen, "Research on induced pluripotent stem cells and the application in ocular tissues," *Int J Ophthalmol.* 8(4): 818-825, Aug. 18, 2015.

Naito et al., "CRISPRdirect: software for designing CRISPR/Cas guide RNA with reduced off-target sites," *Bioinformatics* 31(7): 1120-1123, 2015 (advance access publication on Nov. 20, 2014).

Raab et al., "A Comparative View on Human Somatic Cell Sources for iPSC Generation," Hindawi Publishing Company, *Stem Cells Int.* 2014, Article ID 768391, 2014 (12 pages).

Basma et al., "Differentiation and transplantation of human embryonic stem cell-derived hepatocytes," *Gastroenterology* 136(3): 990-999 (Mar. 2009).

Si-Tayeb et al., "Highly efficient generation of human hepatocyte-like cells from induced pluripotent stem cells," *Hepatology* 51(1): 297-305 (Jan. 2010).

Soto-Gutiérrez et al., "Reversal of mouse hepatic failure using an implanted liver-assist device containing ES cell-derived hepatocytes," *Nature Biotechnology* 24(11):1412-1419 (Nov. 2006).

Zhang et al., "Generation of GFAP::GFP astrocyte reporter lines from human adult fibroblast-derived iPS cells using zinc-finger nuclease technology," *Glia* 64(1): 63-75 (Jan. 2016).

\* cited by examiner

| | Clones picked | Puromycin resistant clones | % success | # clones efficiently activating system | % Efficiency of system activation |
|---|---|---|---|---|---|
| hiPS-TagRFP | 18 | 18 | 100% | 7 | 39% |

FIG. 14A
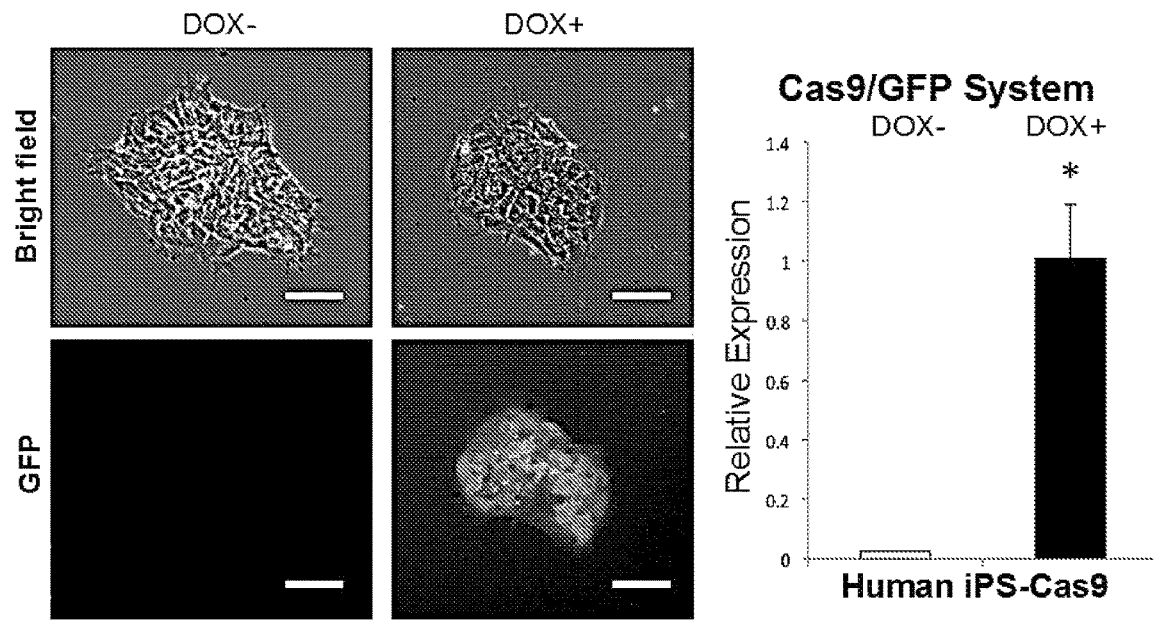
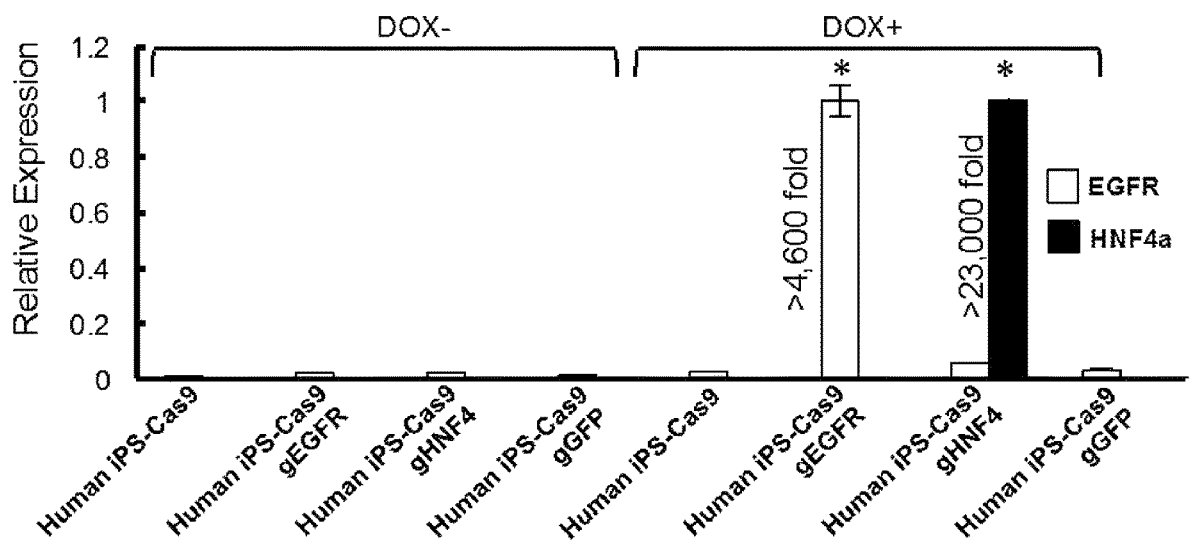
FIG. 14B

# HUMAN INDUCED PLURIPOTENT STEM CELLS FOR HIGH EFFICIENCY GENETIC ENGINEERING

CROSS REFERENCE TO RELATED APPLICATION

This is a § 371 U.S. national stage of International Application No. PCT/US2017/044719, filed Jul. 31, 2017, which was published in English under PCT Article 21(2), and which claims the benefit of U.S. Application No. 62/369,698, filed Aug. 1, 2016, which is incorporated herein by reference.

ACKNOWLEDGMENT OF GOVERNMENT SUPPORT

This invention was made with government support under grant no. DK099257 awarded by the National Institutes of Health. The government has certain rights in the invention.

FIELD

This relates to the field of stem cells, specifically for methods of generating induced pluripotent stem cells containing Cas9, and allowing high efficiency that can be genetic engineering.

BACKGROUND

Patient-specific induced pluripotent stem cells (iPSCs) derived from somatic cells provide a unique tool for the study of human disease, and are a promising source for cell replacement therapies. One crucial limitation has been the inability to perform experiments under genetically defined conditions. This is particularly relevant for late age onset disorders in which in vitro phenotypes are predicted to be subtly susceptible to significant effects of genetic background variations combined with epigenetic alterations. Moreover, there is a clear need for effective therapy strategies for a number of chronic diseases with genetic and epigenetic backgrounds (e.g., nonalcoholic steatohepatitis, alcohol-induced liver disease, aging, Parkinson's disease, heart failure), that require a deep understanding of the mechanisms responsible for the disease's evolution to organ/cell dysfunction in human tissue. Available animal models for these diseases have been extremely useful for elucidating many aspects of the disorders, but the relative roles of the pathways in humans have not been conclusively determined. Most simply stated, mice are not men.

Disclosed herein are high efficiency methods for genome editing in iPSCs. By combining approaches involving genome editing and iPSC technology, generally applicable solutions are provided for addressing such problems by generating sets of isogenic disease and control human pluripotent stem cells.

SUMMARY

Methods are disclosed herein for generating a human induced pluripotent stem cells. The methods include transfecting a human somatic cell with a nucleic acid molecule comprising a doxycycline promoter operably linked to a nucleic acid encoding a Cas9, and constitutive promoter operably linked to a tetracycline responsive element, and inducing the somatic cell to form an induced pluripotent cell. These methods produce induced pluripotent stem cells that can undergo CRISPR/Cas9-mediated recombination at a high efficiency, wherein the human induced pluripotent cells or cells differentiated therefrom are cultured in the presence of doxycycline to induce expression of the Cas9. In some embodiments, the cells are human.

In further embodiments, these cells used to target in any gene of interest by introducing nucleic acids encoding sgRNAs.

Induced pluripotent stem cells produced by these method are also disclosed.

The foregoing and other objects, features, and advantages of the invention will become more apparent from the following detailed description, which proceeds with reference to the accompanying figures.

BRIEF DESCRIPTION OF THE DRAWINGS

FIG. 1A is a schematic of the pcLVI(3G) vector used in conditional systems. FIG. 1B is a schematic diagram of pCLVi(3G)-Tet-ON-3G. The Tet-on-3G system is composed of these two elements: (1) a reverse tetracycline-controlled transactivator inducible promoter (rtTA-3G) expressed constitutively, under the control of an Ubiquitin C promoter; and (2) a Tetracycline Response Element (pTRE-3G) controlling the transcription of a sequence of interest. The pTRE-3G is composed of 7 repeats of the 19 bp bacterial tet-O sequence place upstream of a minimal promoter with very low basal expression in the absence of Tet-On. The rtTA-3G protein binds the pTRE-3G only if bound by a doxycycline. The addition of doxycycline to the system initiates the transcription of the sequence of interest.

FIGS. 14A-14B. Generation and characterization of hiPS-Cas9/GFP. Doxycycline inducible human iPS cells design to carry a Cas9 system specifically for gain of function experiments and a GFP reporter. hiPS-Cas9/GFP displays high expression Cas9 expression and GFP into 100% of cells (A). When nucleofected with sgRNA for EGFR or HNF4 promoters (B), hiPS-Cas9/GFP show a strong increase of either EGFR or HNF4 when Cas9 system is activated, validating high CRISPR/Cas9 activity level of this cell line. Scale bar: 50 um. Data are presented as mean −/+ SEM, with P<0.05.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-96632-05_Sequence-_Listing, Jan. 30, 2019, 16.1 KB], which is incorporated by reference herein. In the accompanying sequence listing:

SEQ ID NO: 1 is an exemplary nucleic acid sequence of a doxycycline promoter.

SEQ ID NO: 2 is an exemplary amino acid sequence of a *Streptococcus pyogenes* Cas9.

SEQ ID NO: 3 is an exemplary nucleic acid sequence of a polynucleotide encoding a tracrRNA.

SEQ ID NO: 4 is an exemplary nucleic acid sequence of a U6 promoter.

SEQ ID NO: 5 is a nucleic acid sequence of a polynucleotide encoding a sgRNA.

SEQ ID NO: 6 is an exemplary nucleic acid sequence of a ubiquitin promoter.

SEQ ID Nos: 7-8 are nucleic acid sequences of a polynucleotides encoding sgRNAs.

SEQ ID NOs: 9-10 are nucleic acid sequences of primers.

DETAILED DESCRIPTION

By combining approach-mediated genome editing and iPSC technology, a generally applicable solution is provided to generate sets of isogenic disease and control human pluripotent stem cells. A schematic approach to generating isogenic disease and custom-engineered pluripotent stem cells has been developed and has involved complex and low efficient methods, as, for example in, FIG. 13.

Figure 2:
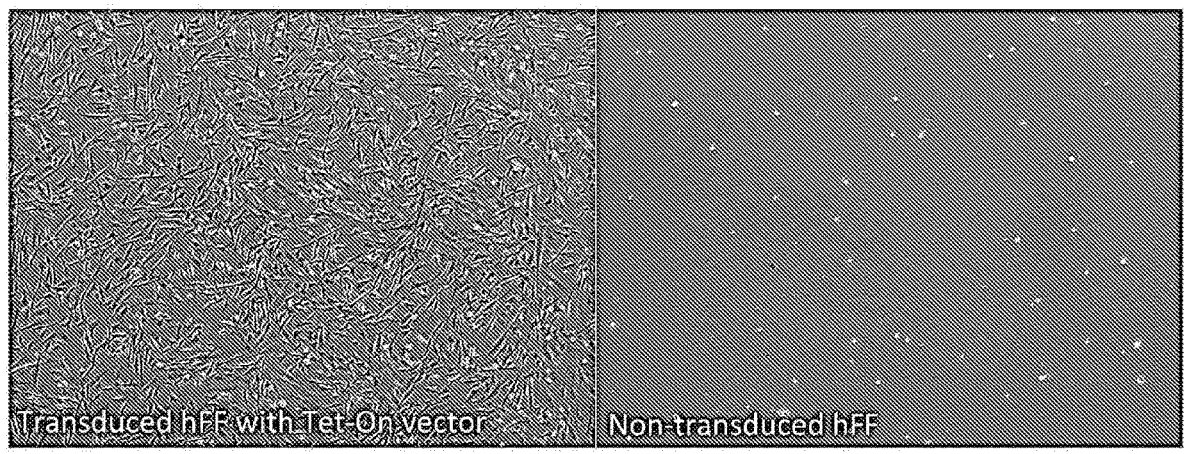
FIG. 2. Bright field microscopy of transduced and non-transduced hFF after 7 days of puromycin selection.

High efficiency methods are disclosed herein for the generation of iPSCs, such as human iPSCs. Disclosed are custom engineered-systems that elucidate the role of transcriptional programs in the development of human disease, at a single and genome wide level. An exemplary protocol is shown in FIG. 2. The robust capability to genetically modify disease-causing point mutations in patient-derived human iPSCs represents a significant advancement for basic biomedical research and an advance toward hiPSC-based cell replacement therapies. Thus, provided is a generally applicable solution to a key problem, and a demonstration of the generation of a panel of isogenic mutant and control cell lines from hiPSCs.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 16, 2015. All references, patent applications and publications, and GENBANK® Accession numbers cited herein are incorporated by reference. In order to facilitate review of the various embodiments of the disclosure, the following explanations of specific terms are provided:

Alter: A change in an effective amount of a substance or parameter of interest, such as a polynucleotide, polypeptide or a property of a cell. An alteration in polypeptide or polynucleotide or enzymatic activity can affect a physiological property of a cell, such as the differentiation, proliferation, or senescence of the cell. The amount of the substance can be changed by a difference in the amount of the substance produced, by a difference in the amount of the substance that has a desired function, or by a difference in the activation of the substance. The change can be an increase or a decrease. The alteration can be in vivo or in vitro. In several embodiments, altering is at least about a 50%, 60%, 70%, 80%, 90%, 95%, 96%, 97%, 98%, 99%, or 100% increase or decrease in the effective amount (level) of a substance, the proliferation and/or survival of a cells, or the activity of a protein, such as an enzyme.

Animal: Living multi-cellular vertebrate organisms, a category that includes, for example, mammals and birds. The term mammal includes both human and non-human mammals. Similarly, the term "subject" includes both human and veterinary subjects.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Clustered regularly interspaced short palindromic repeats (CRISPR) associated protein 9 (Cas9): An RNA-guided DNA endonuclease enzyme associated with the CRISPR (Clustered Regularly Interspersed Palindromic Repeats) adaptive immunity system in *Streptococcus pyogenes*, among other bacteria. Cas9 can cleave nearly any sequence complementary to the guide RNA. Includes Cas9 nucleic acid molecules and proteins. Cas9 sequences are publically available, for example from the GENBANK® sequence database (e.g., GENBANK® Accession Nos. NP_269215.1 and AKS40378.1 provide exemplary Cas9 protein sequences, while GENBANK® Accession No. NC_002737.2 provides an exemplary Cas9 nucleic acid sequence therein). One of ordinary skill in the art can identify additional Cas9 nucleic acid and protein sequences, including Cas9 variants.

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Embryoid Bodies: Three-dimensional aggregates of pluripotent stem cells. These cells can undergo differentiation into cells of the endoderm, mesoderm and ectoderm. In contrast to monolayer cultures, the spheroid structures that are formed when pluripotent stem cells aggregate enables the non-adherent culture of EBs in suspension, which is useful for bioprocessing approaches. The three-dimensional structure, including the establishment of complex cell adhesions and paracrine signaling within the EB microenvironment, enables differentiation and morphogenesis.

Donor polynucleotide: A polynucleotide that is capable of specifically inserting into a genomic locus.

Downstream: A relative position on a polynucleotide, wherein the "downstream" position is closer to the 3' end of the polynucleotide than the reference point. In the instance of a double-stranded polynucleotide, the orientation of 5' and 3' ends are based on the sense strand, as opposed to the antisense strand.

Embryonic stem cells: Embryonic cells derived from the inner cell mass of blastocysts or morulae, optionally that have been serially passaged as cell lines. The term includes cells isolated from one or more blastomeres of an embryo, preferably without destroying the remainder of the embryo. The term also includes cells produced by somatic cell nuclear transfer. "Human embryonic stem cells" (hES cells) includes embryonic cells derived from the inner cell mass of human blastocysts or morulae, optionally that have been serially passaged as cell lines. The hES cells may be derived from fertilization of an egg cell with sperm or DNA, nuclear transfer, parthenogenesis, or by means to generate hES cells with homozygosity in the HLA region. Human ES cells can be produced or derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce an embryonic cell. Human embryonic stem cells include, but are not limited to, MAO1, MAO9, ACT-4, No. 3, H1, H7, H9, H14 and ACT30 embryonic stem cells. Human embryonic stem cells, regardless of their source or the particular method used to produce them, can be identified based on (i) the ability to differentiate into cells of all three germ layers, (ii) expression of at least Oct-4 and alkaline phosphatase, and (iii) ability to produce teratomas when transplanted into immunocompromised animals.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells, but divide to form more cells.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

Feeder layer: Non-proliferating cells (such as irradiated cells) that can be used to support proliferation of stem cells. Protocols for the production of feeder layers are known in the art, and are available on the internet, such as at the National Stem Cell Resource website, which is maintained by the American Type Culture Collection (ATCC).

Growth medium or expansion medium: A synthetic set of culture conditions with the nutrients necessary to support the growth (cell proliferation/expansion) of a specific population of cells. In one embodiment, the cells are stem cells, such as iPSCs. Growth media generally include a carbon source, a nitrogen source and a buffer to maintain pH. In one embodiment, growth medium contains a minimal essential media, such as DMEM, supplemented with various nutrients to enhance stem cell growth. Additionally, the minimal essential media may be supplemented with additives such as horse, calf or fetal bovine serum.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An "isolated" biological component, such as a nucleic acid, protein or organelle that has been substantially separated or purified away from other biological components in the environment (such as a cell) in which the component naturally occurs, i.e., chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Similarly, an "isolated" cell has been substantially separated, produced apart from, or purified away from other cells of the organism in which the cell naturally occurs. Isolated cells can be, for example, at least 99%, at least 98%, at least 97%, at least 96%, 95%, at least 94%, at least 93%, at least 92%, or at least 90% pure.

Mammal: This term includes both human and non-human mammals. Examples of mammals include, but are not limited to: humans and veterinary and laboratory animals, such as pigs, cows, goats, cats, dogs, rabbits and mice.

Marker or Label: An agent capable of detection, for example by ELISA, spectrophotometry, flow cytometry, immunohistochemistry, immunofluorescence, microscopy, Northern analysis or Southern analysis. For example, a marker can be attached to a nucleic acid molecule or protein, thereby permitting detection of the nucleic acid molecule or protein. Examples of markers include, but are not limited to, radioactive isotopes, nitroimidazoles, enzyme substrates, co-factors, ligands, chemiluminescent agents, fluorophores, haptens, enzymes, and combinations thereof. Methods for labeling and guidance in the choice of markers appropriate for various purposes are discussed for example in Sambrook et al. (Molecular Cloning: A Laboratory Manual, Cold Spring Harbor, NY, 1989) and Ausubel et al. (In Current Protocols in Molecular Biology, John Wiley & Sons, New York, 1998).

In some embodiments, the marker is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pluripotent stem cells: Stem cells that: (a) are capable of inducing teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc), but that cannot form an embryo and the extraembryonic membranes (are not totipotent).

Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). These embryonic stem cells can be generated from embryonic material produced by fertilization or by asexual means, including somatic cell nuclear transfer (SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro).

Pluripotent stem cells also include "induced pluripotent stem cells (iPSCs)" generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell. iPSCs are similar in properties to embryonic stem cells.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: Three or more covalently attached amino acids. The term encompasses proteins, protein fragments, and protein domains. A "DNA-binding" polypeptide is a polypeptide with the ability to specifically bind DNA.

The term "polypeptide" is specifically intended to cover naturally occurring proteins, as well as those which are recombinantly or synthetically produced. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A promoter can be a constitutively active promoter (i.e., a promoter that is constitutively in an active/"ON" state), an inducible promoter (i.e., a promoter whose state, active/"ON" or inactive/"OFF", is controlled by an external stimulus, e.g., the presence of a particular temperature, compound, or protein), a spatially restricted promoter (e.g., tissue specific promoter, cell type specific promoter, etc.), or it may be a temporally restricted promoter (i.e., the promoter is in the "ON" state or "OFF" state during specific stages of embryonic development or during specific stages of a biological process, e.g., hair follicle cycle in mice).

Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, steroid-regulated promoters, metal-regulated promoters, estrogen receptor-regulated promoter, etc. Inducible promoters can be regulated by molecules including, but not limited to, doxycycline; RNA polymerase, e.g., T7 RNA polymerase; an estrogen receptor; an estrogen receptor fusion; etc.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. A purified population of nucleic acids or proteins is greater than about 90%, 91%, 92%, 93%, 94%, 95%, 96%, 97%, 98%, 99% or 100% pure, or free other nucleic acids or proteins, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Recombination: A process of exchange of genetic information between two polynucleotides. "Homologous recombination (HR)" refers to the specialized form of an exchange that takes place, for example, during repair of double-strand breaks in cells. Nucleotide sequence homology is utilized in recombination, for example using a "donor" molecule to template repair of a "target" molecule (i.e., the one that experienced the double-strand break), and is variously known as "non-crossover gene conversion" or "short tract gene conversion," because it leads to the transfer of genetic information from the donor to the target. "Recombination efficiency" is the rate and effectiveness of recombination a particular host cells, such as an iPSC.

Enzyme mismatch cleavage assays can be used to quantify the efficiency of mutations induced by Cas9, namely, T7E1 and Surveyor. This test shows the percent of insertion or deletion of bases in the DNA (Indels) (see Zhou et al., Nature. 2014 May 22; 509(7501):487-91, incorporated herein by reference). In this system, 9-50% of indels efficiency is considered as high rate efficiency recombination.

A widely used method to identify mutations is the T7 Endonuclease I (T7E1) mutation detection assay. This assay detects heteroduplex DNA that results from the annealing of a DNA strand, including desired mutations, with a wildtype DNA strand. In some embodiments, this assay is used to quantify the efficiency of mutations induced by Cas9. (see Zhou et al., Nature. 2014 May 22; 509(7501):487-91, incorporated herein by reference).

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a FGF polypeptide will possess a relatively high degree of sequence identity when aligned using standard methods.

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul, et al., *Nature Genet.,* 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, sequence identity counted over the full length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Short Guide RNA (gRNA): Short guide RNA used in conjunction with CRISPR associated systems (Cas). sgRNAs contains nucleotides of sequence complementary to the desired target site. Watson-crick pairing of the sgRNA with the target site recruits the nuclease-deficient Cas9 to bind the DNA at that locus.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Transgene: An exogenous gene.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Undifferentiated: Cells that display characteristic markers and morphological characteristics of undifferentiated cells, distinguishing them from differentiated cells of embryo or adult origin. Thus, in some embodiments, undifferentiated cells do not express cell lineage specific markers.

Upstream: A relative position on a polynucleotide, wherein the "upstream" position is closer to the 5' end of the polynucleotide than the reference point. In the instance of a double-stranded polynucleotide, the orientation of 5' and 3' ends are based on the sense strand, as opposed to the antisense strand.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

"Lentiviral vector" refers to a gene delivery vehicle adapted from lentiviruses, a subclass of Retroviruses. Lentiviruses have recently been adapted as gene delivery vehicles (vectors) thanks to their ability to integrate into the genome of non-dividing cells, which is the unique feature of lentiviruses as other retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. Generally, lentiviral vectors do not include the genes required for their replication, and thus are "replication defective." To produce a lentivirus, several plasmids are transfected into a so-called packaging cell line, for example HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the φ (psi) sequence. This sequence is used to package the genome into the virion.

Virus: Microscopic infectious organism that reproduces inside living cells. A virus consists essentially of a core of a single nucleic acid surrounded by a protein coat and has the ability to replicate only inside a living cell. "Viral replication" is the production of additional virus by the occurrence of at least one viral life cycle. Viral vectors are known in the art, and include, for example, adenovirus, AAV, lentivirus and herpes virus.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Methods for Producing Induced Pluripotent Stem Cells (iPSC)

iPSC cells can be indefinitely maintained in vitro in an undifferentiated state and yet are capable of differentiating into virtually any cell type. Methods are provided herein wherein somatic cells are used to prepare induced pluripotent stem cells that are highly efficient for knock-in and/or knock out of one or more genes of interest. Disclosed herein are methods to induce the production of these iPSC, such as human iPSC.

Somatic Cells

The starting somatic cell can be any cell of interest. Any cells other than germ cells of mammalian origin (such as, humans, mice, monkeys, pigs, rats etc.) can be used as starting material for the production of iPSCs. In one embodiment, the stem cells are human Examples include keratinizing epithelial cells, mucosal epithelial cells, exocrine gland epithelial cells, endocrine cells, liver cells, epithelial cells, endothelial cells, fibroblasts, muscle cells, cells of the blood and the immune system, cells of the nervous system including nerve cells and glia cells, pigment cells, and progenitor cells, including hematopoietic stem cells, amongst others. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. The somatic cell can be an adult or a fetal cell. In a specific non-limiting example, the somatic cell is a fibroblast. In another specific non-limiting example, the somatic cell is a hepatocyte.

The choice of mammalian individuals as a source of somatic cells is not particularly limited. Allogenic cells can be used, if the resulting cells will be transplanted into a subject. Thus, in some embodiments, the iPSCs are not matched for MHC (e.g., HLA) to a subject. In some embodiments, when the iPSCs obtained are to be used for regenerative medicine in humans, cells can be collected from the somatic cells from the subject to be treated, or another subject with the same or substantially the same HLA type as that of the patient. Thus, the stem cells can be autologous or substantially the same HLA type. "Substantially the same HLA type" indicates that the HLA type of donor matches with that of a patient to the extent that the transplanted cells, which have been obtained by inducing differentiation of iPSCs derived from the donor's somatic cells, can be engrafted when they are transplanted to the subject. The subject optionally can be treated with an immunosuppressant. In one example, it includes an HLA type wherein major HLAs (e.g., the three major loci of HLA-A, HLA-B and HLA-DR, the four major loci further including HLA-Cw) are identical.

Somatic cells isolated from a mammal can be pre-cultured using a medium known to be suitable for their cultivation according to the choice of cells before being subjected to the step of nuclear reprogramming Specific non-limiting examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. One of skill in the art can readily ascertain appropriate tissue culture conditions to propagate particular cell types from a mammal, such as a human. In some embodiments, to obtain completely xeno-free human iPSCs, the medium can exclude ingredients derived from non-human animals, such as FCS. Media comprising a basal medium supplemented with human-derived ingredients suitable for cultivation of various somatic cells (particularly, recombinant human proteins such as growth factors), non-essential amino acids, vitamins and the like are commercially available; those skilled in the art are able to choose an appropriate xeno-free medium according to the source of somatic cells. Somatic cells pre-cultured using a xeno-free medium are dissociated from the culture vessel using an appropriate xeno-free cell dissociation solution, and recovered, after which they are brought into contact with nuclear reprogramming substances.

Generally, cells are cultured at about 35 to 38° C., usually at 37° C., in about 4-6% $CO_2$, generally at 5% $CO_2$, unless specifically indicated otherwise below.

Constructs Including a Doxycycline Inducible Promoter Operably Linked to a Nucleic Acid Molecule Encoding Cas9

In some embodiments, the somatic cells is transfected to introduce a nucleic acid molecule including a doxycycline promoter operably linked to a nucleic acid encoding Cas9. One skilled in the art will recognize that any Cas9 protein can be used in the systems and methods disclosed herein. This promoter provides for inducible expression of Cas9. In a Tet-On system, the rtTA protein is capable of binding the operator (the doxycycline promoter) only if bound by a tetracycline. Thus, the promoter is activated by doxycycline. The systems disclosed herein utilize an inducible expression platform based on 3G TET technology. An exemplary nucleic acid sequence of this promoter is shown below (SEQ ID NO: 1).

```
                                         (SEQ ID NO: 1)
ATCGATACTAGACTCGAGTTTACTCCCTATCAGTGATAGAGAACGTATGA

AGAGTTTACTCCCTATCAGTGATAGAGAACGTATGCAGACTTTACTCCCT

ATCAGTGATAGAGAACGTATAAGGAGTTTACTCCCTATCAGTGATAGAGA

ACGTATGACCAGTTTACTCCCTATCAGTGATAGAGAACGTATCTACAGTT

TACTCCCTATCAGTGATAGAGAACGTATATCCAGTTTACTCCCTATCAGT

GATAGAGAACGTATAAGCTTTAGGCGTGTACGGTGGGCGCCTATAAAAGC

AGAGCTCGTTTAGTGAACCGTCAGATCGCCTGGA
```

Variants of this nucleic acid sequence can also be used, such as nucleic acid sequences at least 90%, 91%, 92%, 935, 94%, 95%, 96%, 97%, 98% or 99% sequence identical to SEQ ID NO: 1, provided the nucleic acid sequence functions as a doxycycline inducible promoter.

Figure 1A:
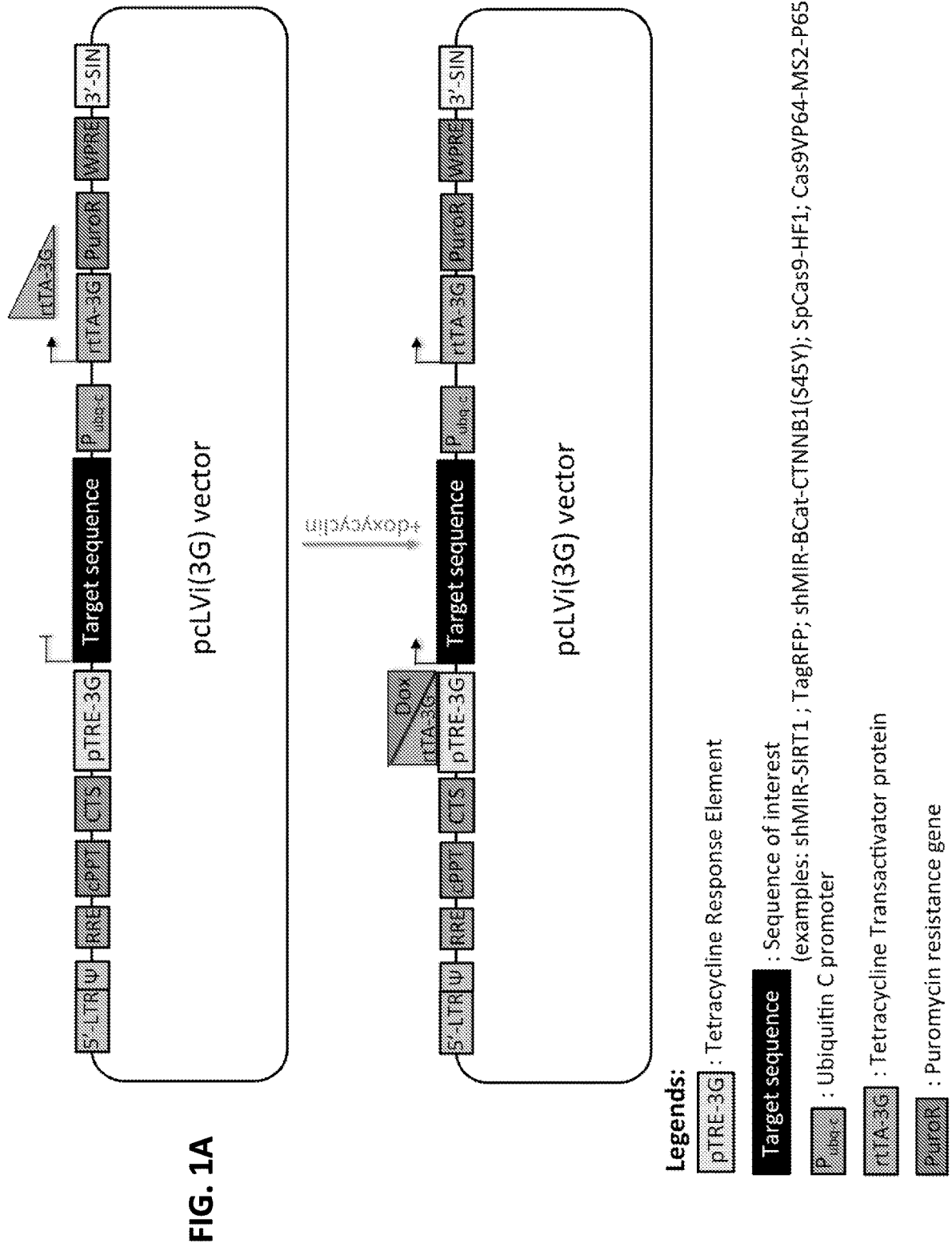
FIGS. 1A-1B.
Figure 1B:
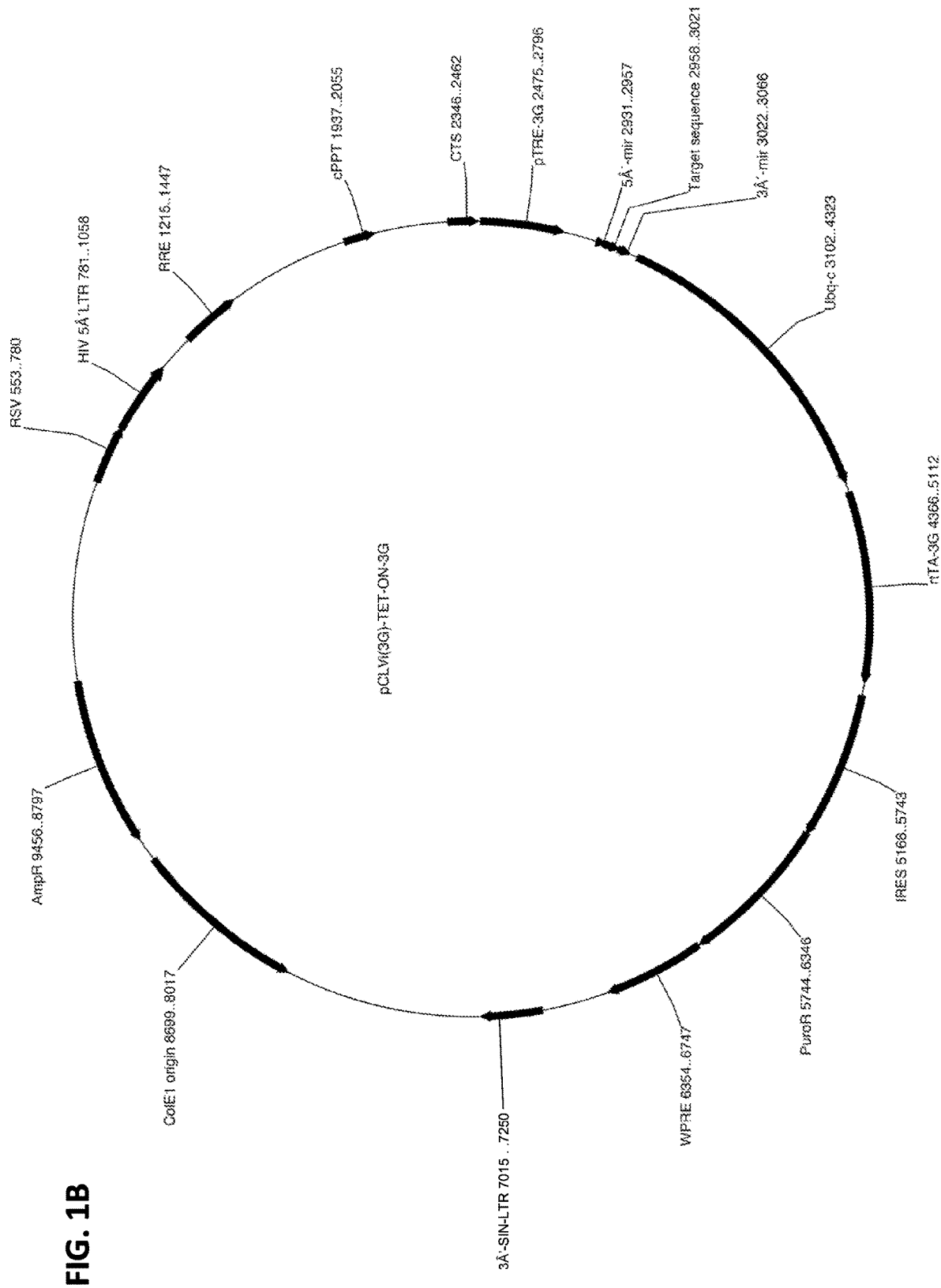

A doxycycline inducible promoter is a highly sensitive and provides transcription without leakiness. Inducible genetic engineering can be used, using the method disclosed herein, to produce a knockdown, knockin or dual knockins-knockdowns in genes of interest. One form of a doxycycline inducible promoter is the Tet-on-3G system; this system is of use in the methods disclosed herein. This system is composed of these two elements: (1) a reverse tetracycline-controlled transactivator inducible promoter (rtTA) expressed constitutively, under the control of a promoter, such as a Ubiquitin C promoter; (2) a Tetracycline Response Element (TRE) controlling the transcription of a sequence of interest. In some embodiments, the TRE is composed of 7 repeats of the 19 bp bacterial tet-O sequence placed upstream of a minimal promoter with very low basal expression in the absence of Tet-On. The rtTA protein binds the TRE only if bound by a doxycycline. The addition of doxycycline to the system initiates the transcription of the sequence of interest (fluorescent reporter genes; Cas9 etc.). An exemplary construct is shown in FIG. 1. Additional suitable promoters are disclosed, for example, in Published U.S. Patent Application No. 2014/0107190, which is incorporated herein by reference. Thus, in some embodiments, the somatic cell includes a construct encoding the rtTA protein, and a TRE controlling the transcription of Cas9. Tetracycline/doxycycline inducible promoters are disclosed, for example, in U.S. Pat. Nos. 5,464,758; 5,851,796; 5,912, 411; and 6,000,494, all incorporated by reference herein. Any of these promoters are of use in the methods disclosed herein.

In some embodiments, a doxycycline inducible promoter operably linked to Cas9 is introduced into the somatic cell. One Cas9 of use is from *Streptococcus pyogenes* as depicted in SEQ ID NO. 2 below.

(SEQ ID NO: 2)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NPFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

Variants of this amino acid sequence can also be used, such as amino acid sequences at least 90%, 91%, 92%, 935, 94%, 95%, 96%, 97%, 98% or 99% sequence identical to SEQ ID NO: 2, provided the nucleic acid sequence functions as a Cas9 polypeptide. In some embodiments, the variant includes at most 1, 2, 3, 4, 5, 6, 7, 8, 9 or 10 conservative amino acid substitutions in SEQ ID NO: 2.

In other embodiments, the *Streptococcus pyogenes* Cas9 peptide can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M et al. Science. 2012 Aug. 17; 337(6096):816-21; and Jinek M. et al. Science. 2014 Mar. 14; 343 (6176). Thus in some embodiments the systems and methods disclosed herein can be used with the wild type Cas9 protein having double-stranded nuclease activity, Cas9 mutants that act as single stranded nickases, or other mutants with modified nuclease activity.

The Cas9 peptide can be an activating Cas9 (Cas9a). Suitable Cas9 sequences include SpCas9-HF1, dCas9-VP64. Suitable Cas9 molecules are disclosed, for example, in Chavez et al., Nat. Methods 12: 326-328, Oct. 1, 2015, which is incorporated herein by reference. Optionally, a synergistic activator can be encoded with the Cas9, see the internet, sam.genome-engineering.org, incorporated herein by reference.

CRISPR-Cas9 uses a short guide RNA (sgRNA) to direct nuclease Cas9 to the target site and generate double-strand breaks, stimulating DNA repair processes that give rise to DNA editing. To circumvent off targets effects, a modified Cas9 can be utilized, without any reported off target effect (SpCas9-HF1). SpCas9-HF1 enables loss, but also gain of function, provided that the desired template sequence is delivered and used by the Homology Directed Repair cell machinery. Additionally, SpCas9-HF1 can be used for whole genome loss-of-function screening using sgRNA libraries. To enable gain-of-function for whole genome screening, a CRISPR-Cas9 Synergistic Activation Mediator (SAM) complex can be used. This is a protein complex composed of an inactive Cas9-VP64 fusion and activation helper proteins (MS2-P65-HSF1). This complex interacts with sgRNA to ensure robust transcriptional activation of target genes. This system can be used in the present methods for gain-of-function screening.

Cas9 can be used for inhibiting genes (Cas9i). This is a catalytically active Cas9 that, when guided with sgRNA, will induce loss of function by site-specifically cleavage of double-stranded DNA, resulting in the activation of the doublestrand break (DSB) repair machinery. Thus, use of Cas9 results in loss of gene function. A single or a library of gRNA can be used for loss-of-function screens. CRISPR knockout libraries or single gRNA render genes non-functional by inducing insertions or deletions in targeted genes.

The Cas9 includes a catalytically active nuclease domain. In some embodiments, the Cas9 nuclease includes an HNH-like endonuclease and a RuvC-like endonuclease. Thus in some embodiments, to generate a double-stranded DNA break, the HNH-like endonuclease cleaves the DNA strand complementary to the sgRNA, and the RuvC-like domain cleaves the non-complementary DNA strand. A Cas9 endonuclease can be guided to specific genomic targets using specific sgRNA (see below).

Optionally, a nucleic acid molecule encoding a marker also can be operably linked to the doxycycline inducible promoter, or to another promoter. Markers include, but are not limited to, enzymes and fluorescent proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the promoter. In addition, other genes can be included, such as genes that may influence stem cell to differentiate, or influence function, or physiology.

In specific non-limiting examples, the marker is tdTomato fluorescent protein or green fluorescent protein. In other embodiments, a nucleic acid molecule encoding a marker is not operably linked the doxycycline promoter.

In some embodiments, the doxycycline promoter operably linked to the nucleic acid encoding Cas9 are included in a vector. Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in E. coli, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids of use are composed of: (1) a high copy number replication origin, (2) a selectable marker, such as, but not limited to, the neo gene for antibiotic selection, such as with kanamycin, puromycin, neomycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

Viral vectors can be utilized for the introduction of nucleic acids, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377), human herpesvirus vectors (HHV) such as HHV-6 and HHV-7, and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors can be used. Vectors can be obtained from commercial sources (such as PharMingen, San Diego, Calif.; Protein Sciences Corp., Meriden, Conn.; Stratagene, La Jolla, Calif.). Suitable vectors are disclosed, for example, in U.S. Published Patent Application No. 2010/0247486, which is incorporated herein by reference. In specific non-limiting examples, the vectors are retrovirus vectors (for example, lentivirus vectors), measles virus vectors, alphavirus vectors, baculovirus vectors, Sindbis virus vectors, adenovirus and poliovirus vectors.

In some embodiments, the vector is a lentiviral vector. An advantage of lentiviruses for infection of cells is the ability for sustained transgene expression. Leintiviruses include, but are not limited to, Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). Lentiviral vectors are well known in the art (see, for example, Naldini et al., Science, 272(5259):263-267, 1996; Zufferey et al., Nat Biotechnol, 15(9):871-875, 1997; Blomer et al., J Virol, 71(9):6641-6649, 1997; U.S. Pat. Nos. 6,013,516 and 5,994,136). Recombinant lentiviral vectors are capable of infecting non-dividing cells and can be used for both in vivo and in vitro gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

A recombinant lentivirus can be targeted to a specific cell type by linkage of the envelope protein with an antibody or a particular ligand for targeting to a receptor of a particular cell-type. A sequence (including a regulatory region) of interest is inserted into the viral vector, along with another gene which encodes the ligand for a receptor on a specific target cell, in order to produce a target-specific vector. The recombinant lentiviruses can be genetically modified in such a way that certain genes constituting the native infectious virus are eliminated and replaced with a nucleic acid sequence of interest to be introduced into the target cells.

In some embodiments, a lentiviral vector can integrate into the genome of the host cell. The genetic material thus transferred is then transcribed and possibly translated into proteins inside the host cell. In other embodiments, a lentiviral vector is a non integrative lentiviral vector, such that the vector is present in episomal forms.

The lentiviral vector can further comprise additional elements which help to improve expression of the genes encoded within the vector. Regions required for the integration of the vector into the genome of the target cell such as the Long-terminal repeats (LTRs). Thus, a lentiviral vector can include a 5' LTR and a 3' LTR. "5' LTR" refers to a 5' retroviral or lentiviral long terminal repeat, which may or may not be modified from its corresponding native 5' LTR by deleting and/or mutating endogenous sequences and/or adding heterologous sequences. The 5' LTR may be natural or synthetic. "3' LTR" refers to a 3' retroviral or lentiviral long terminal repeat, which may or may not be modified from its corresponding native (i.e., that existing in the wild-type retrovirus) 3' LTR by deleting and/or mutating endogenous sequences and/or adding heterologous sequences. The 3' LTR may be natural or synthetic.

An encapsidation sequence such as the lentiviral Psi (ψ) sequence can be included in the vector. In some embodiments, sequences enhancing the RNA nuclear export, such as the sequence comprising the HIV-1 REV response element (RRE) sequence, can be included in the vector. Another sequence that enhances the RNA nuclear export is the CTE sequence (Oh et al, 2007, Retrovirology. 2007 Jun. 5; 4:38). These sequences are also useful for determining the copy number of the integrated lentiviral vectors. Other sequences that enhance DNA nuclear import are lentiviral cPPT CTS sequences from HIV-2, SIV, FIV, EIAV, BIV, VISNA and CAEV. Any of these sequences can be included in the vector.

In another embodiment the lentiviral vector is another form of self-inactivating (SIN) vector as a result of a deletion in the 3' long terminal repeat region (LTR). In some examples, the vector contains a deletion within the viral promoter. The LTR of lentiviruses such as the HIV LTR contains a viral promoter. Although this promoter is relatively inefficient, when transactivated by e.g. tat, the promoter is efficient because tat-mediated transactivation increases the rate of transcription about 100 fold. In some circumstances, the presence of the viral promoter can interfere with transcription of heterologous promoters operably linked to a transgene. To minimize such interference and better regulate the expression of transgenes, the lentiviral promoter may be deleted.

In some embodiments, the lentiviral vector comprises, in the 5' to 3' orientation: the 5' LTR (wild-type or modified), A Rev response element (RRE), a c polypurine tract (cPPT), the transcriptional regulatory region, the doxycycline promoter linked to Cas9, an optional transcriptional regulation element, and the 3' LTR.

Methods of transfection of DNA include calcium phosphate coprecipitates, conventional mechanical procedures such as microinjection, electroporation, insertion of a plasmid encased in liposomes, or virus vectors.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins.

Reprogramming

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, all of which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 2012/0196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HPV16 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

After being cultured with nuclear reprogramming substances, the cell can, for example, be cultured under conditions suitable for culturing stem cells. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

In some embodiments, the cell is cultured in the co-presence of mouse embryonic fibroblasts treated with radiation or an antibiotic to terminate the cell division, as feeder cells. Mouse embryonic fibroblasts in common use as feeders include the STO cell line (ATCC CRL-1503) and the like; for induction of an iPSC, useful cells can be generated by stably integrating the neomycin resistance gene and the LIF gene in the STO cell (SNL76/7 STO cell; ECACC 07032801) (McMahon, A. P. & Bradley, A. Cell 62, 1073-1085, 1990) and the like can be used. Mitomycin C-treated MEFs are commercially available from Millipore. Gamma-irradiated MEFs are commercially available from Global Stem Generally, somatic cells are transduced with reprogramming factors in the absence of MEFs. In some embodiments, about 7 to eight days after transduction, the cells are re-seeded onto MEFs.

The expression of a key pluripotency factor, NANOG, and embryonic stem cell specific surface antigens (SSEA-3, SSEA-4, TRA1-60, TRA1-81) have been routinely used to identify fully reprogrammed human cells. At the functional level, iPSCs also demonstrate the ability to differentiate into lineages from all three embryonic germ layers.

In some embodiments, upon inducing the somatic cells to produce the human iPSC, more than 10% of the human induced pluripotent stem cells express the Cas9 when the cells are exposed to doxycycline. In additional embodiments, more than about 15%, about 20%, about 25%, about 30%, about 35%, about 40%, about 45%, or about 50% of the human induced pluripotent stem cells express the Cas9 when the cells are exposed to doxycycline. In specific non-limiting examples, about 35% to about 45% of the human induced pluripotent stem cells express the Cas9 when the cells are exposed to doxycycline, such as about 38% to about 42%, such as about 40%. In this context, "about" indicates within one percent. In other embodiments, more than 15%, 20%, 25%, 30%, 35%, 40%, 45% or 50% of the human induced pluripotent stem cell clones or colonies express the Cas9 when the cells are exposed to doxycycline. In specific non-limiting examples, 35% to 45% of the human induced pluripotent stem cell clones or colonies express the Cas9 when the cells are exposed to doxycycline, such as 38% to 42%, such as 40%.

Differentiation of iPSC

The iPSC can be differentiated into any cell type of interest. Appropriate differentiated cells (of ectodermal, mesodermal or endodermal lineage) can be produced. These cells are of use in modeling simple and complex diseases and for treatment in a variety of forms. For treatment, the mode of administration can be determined by a person of skill in the art depending on the type of organ/injury to be treated. For example, iPSCs or differentiated cells derived therefrom, may be administered by injection (as a suspension) or implanted on a biodegradable matrix.

In some embodiments, iPSCs can be differentiated into neurons, such as adrenergic or dopaminergic neurons. The iPS cells thus established can be used for various purposes. For example, by utilizing a method of differentiation iPSC can be differentiated into pancreatic stem-like cells, hematopoietic cells, myocardial cells, myofibroblasts, blood cells, vascular endothelial cells, insulin-secreting cells and liver cells, see for example, U.S. Published Patent Application No. 2015/0252330, incorporated herein by reference. Additional methods are disclosed, for example, in U.S. Published Patent Application No. 2016/0083715, U.S. Published Patent Application No. 2015/0368713, U.S. Published Patent Application No. 2015/0159133, U.S. Published Patent Application No. 2014/0356951, U.S. Published Patent Application No. 2013/0295064, which are incorporated herein by reference. In one non-limiting example, the iPSC are differentiated into hepatocytes.

CRISPR Cas9 Recombination

In some embodiments, the methods also include introducing nucleic acids encoding guide RNAs (gRNAs). In some embodiments, the methods disclosed herein can include introducing the nucleic acid encoding the sgRNAs into the somatic cell, prior to inducing formation of an iPSC. In other embodiments, the methods disclosed herein can include introducing the nucleic acid encoding the sgRNAs into an iPSC including the doxycycline promoter operably linked to Cas9. In further embodiments, the methods disclosed herein can include introducing the nucleic acid encoding the sgRNAs into a differentiated cell, after inducing the iPSC (including the doxycycline promoter operably linked to Cas9) to differentiate.

The nucleic acid encoding the sgRNA can be linked to a constitutive promoter. Suitable promoters include, but are not limited to, the U6 promoter or the ubiquitin promoter.

```
                                              (SEQ ID NO: 6)
CGATACAAGGCTGTTAGAGAGATAATTAGAATTAATTTGACTGTAAACAC

AAAGATATTAGTACAAAATACGTGACGTAGAAAGTAATAATTTCTTGGGT

AGTTTGCAGTTTTAAAATTATGTTTTAAAATGGACTATCATATGCTTACC

GTAACTTGAAAGTATTTCGATTTCTTGGCTTTATATATCTTGTGGAAAGG

ACGAAACACCGGAGACGGTTGTAAATGAGCACACAAAATACACATGCTAA

AATATTATATTCTATGACCTTTATAAAATCAACCAAAATCTTCTTTTTAA

TAACTTTAGTATCAATAATTAGAATTTTTATGTTCCTTTTTGCAAACTTT

TAATAAAAATGAGCAAAATAAAAAAACGCTAGTTTTAGTAACTCGCGTTG

TTTTCTTCACCTTTAATAATAGCTACTCCACCACTTGTTCCTAAGCGGTC

AGCTCCTGCTTCAATCATTTTTTGAGCATCTTCAAATGTTCTAACTCCAC

CAGCTGCTTTAACTAAAGCATTGTCTTTAACAACTGACTTCATTAGTTTA

ACATCTTCAAATGTTGCACCTGATTTTGAAAATCCTGTTGATGTTTTAAC

AAATTCTAATCCAGCTTCAACAGCTATTTCACAAGCTTTCATGATTTCTT

CTTTTGTTAATAAACAATTTTCCATAATACATTTAACAACATGTGATCCA

GCTGCTTTTTTTACAGCTTTCATGTCTTCTAAAACTAATTCATAATTTTT

GTCTTTTAATGCACCAATATTTAATACCATATCAATTTCTGTTGCACCAT

CTTTAATTGCTTCAGAAACTTCGAATGCTTTTGTAGCTGTTGTGCATGCA

CCTAGAGGAAAACCTACAACATTTGTTATTCCTACATTTGTGCCTTTTAA

TAATTCTTTACAATAGCTTGTTCAATATGAATTAACACAAACTGTTGCAA

AATCAAATTCAATTGC
```

Variants of this nucleic acid sequence can also be used, such as nucleic acid sequences at least 90%, 91%, 92%, 935, 94%, 95%, 96%, 97%, 98% or 99% sequence identical to SEQ ID NO: 2, provided the nucleic acid sequence functions as a promoter. In some embodiments, primers are used when sequencing nucleic acids encoding sgRNAs into an iPSC or into a cell differentiated from the iPSC. These primers include, but are not limited to:

```
    hU6-F:
                                              (SEQ ID NO: 9)
    5'-GAGGGCCTATTTCCCATGATT-3'

LKO.1 5':
                                              (SEQ ID NO: 10)
    5'-GACTATCATATGCTTACCGT-3'
```

In other embodiments, an inducible promoter is utilized, and the sgRNAs are introduced into the starting somatic cell.

The sgRNA can also be introduced into cells differentiated from the iPSC. When recombination is desired, expression can, in some circumstances, be induced from this inducible promoter. Thus, expression can be induced in the starting somatic cells, iPSCs, or cells differentiated from the iPSCs. These promoters include, but are not limited to:

guide sequence (e.g. sgRNA) which preserves the ability to direct sequence-specific Cas9 dsDNA cleavage (see Jinek, M., et. al., Science. 17 Aug. 2012:337; 816-821). In some embodiments, the Cas9-guide sequence complex results in cleavage of one or both strands at a target sequence within a gene of interest. Thus, the Cas9 endonuclease (Jinek, M.,

| Target tissue | Promoter | Vector | Transgene | References |
|---|---|---|---|---|
| LIVER | Apo A-I | Ad | Apo A-I | [De Geest et al., 2000] |
| | ApoE | HCAd | ApoE | [Kim et al., 2001] |
| | $\alpha_1$-antitrypsin (hAAT) | Ad | Apo A-I | [Van Linthout et al., 2002] |
| | | HCAd | hAAT | [Schiedner et al., 1998][Scheidner et al., 2002] |
| | | Plasmid | factorIX | [Miao et al., 2001][Eluhardt et al., 2002] |
| | hAAT & Apo A-I | Retroviral | hAAT | [Okuyama, 1996] |
| | Transthyretin | HCAd | hGH | [Burcin et al., 1999] |
| | Liver-enriched activator | Transgenic | LUC | [Kistner et al., 1996] |
| | Albumin | HCAd | FactorVIII | [Reddy et al., 2002] |
| | | Lentivirus | factorIX | [Follenzi et al., 2002] |
| | Phosphoenolpyruvate carboxykinase (PEPCK) | HCAd | VLDLR | [Oka et al., 2001] |
| | $RNAP_n$ promoter | Retrovirus | hAAT | [Rettinger et al., 1994] |
| ENDOTHELIUM | PAI-1 | AAV | Thrombomodulin | [Mimar J, 2001] |
| | ICAM-2, Endoglin | Plasmid | Endoglin | [Velasco et al., 2001] |
| | ICAM-2, flt-1, vWF | Ad | lacZ | [Nicklin et al., 2001] |
| MUSCLE | MCK | Ad | LacZ, LUC | [Hauser et al., 2001][Larochelle et al., 2002] |
| | | Plasmid | hBSAg | [Weeratns et al., 2001] |
| | | Ad/AAV | γ-surcoglycan | [Cordier et al., 2000] |
| | SMC α-actin | Plasmid | LUC | [Keogh et al., 1999][Prentice et al., 1997] |
| | | Ad | Rb/E2F hybrid | [Wills et al., 2001] |
| | | Ad | GFP, lacZ, IFNγ | [Ribault et al., 2001] |
| | | AAV | Factor IX | [Hagstrom et al., 2000] |
| | Myosin heavy-chain | Plasmid | CAT | [Skarli et al., 1998] |
| | | AAV | lacZ, hGH | [Aikawa et al., 2002] |
| | Myosin light-chain | Ad | LacZ, LUC | [Griscelli et al., 1998][Franz et al., 1997] |
| | | AAV | GFP, antisense | [Phillips et al., 2002] |
| EPITHELIUM | Cytokeratin 18 | Plasmid | LacZ, CFTR | [Chow et al., 1997][Koehler et al., 2001] |
| | CFTR | Ad | LacZ, LUC | [Imler et al., 1996][Suzuki et al., 1996] |
| NEURONAL | GFAP, NSE, Synapsin I, Preproenkephalin, | Ad | LacZ, GFP | [Smith-Arica et al., 2000][Glover et al., 2002] |
| | | AAV | LUC, GFP | [Xu et al., 2001] |
| | Dopamine β-hydroxylase (dβH) | Plasmid, Ad | CAT, GFP, lacZ | [Hwang et al., 2001] |
| | Prolactin | Ad | LacZ, HSV-tk | [Southgate et al., 2000] |
| | Myelin basic protein | AAV | GFP | [Chen et al., 1998] |
| ERYTHROID | Ankyrin | Retrovirus | γ-globin | [Sabatino et al., 2001] |
| | | Lentivirus | ferrochelatase | [Richard et al., 2001] |
| | α-spectrin, Globin | Lentivirus | GFP, β/γ-globin | [Moreau-Gaudry et al., 2001] |
| | HLA-DRα | Lentivirus | GFP | [Cui et al., 2002] |
| | CD4 | Retroviral | GFP | [Zhao-Emonet JC, 2000] |
| | Dectin-2 | Plasmid | GFP, LUC | [Morita et al., 2001] |

ABBREVIATIONS:
PAI-1, plasminogen activator inhibitor I;
ICAM-2, Intercellular adhesion molecule2;
flt-1, fms-like tyrosine kinase-J;
vWF, von-Willebrand factor;
MCK, muscle creatine kinase;
CFTR, cystic fibrosis transmembrane conductance regulator;
GFAP, glial fibrillary acidic protein;
NSE, neumoral-specific endolase;
LUC, luciferase;
GFP, green flourescens protein;
HSV-tk, herpes simplex virus thymidine kinase.

Table from Papadkis et al., Current Gene Therapy 4: 89-113, 2004, incorporated herein by reference. One of skill in the art can readily identify promoters of use.

The promoter can be a constitutive promoter, such as, but not limited to, the ubiquitin promoter, see below.

The Cas9 RNA guide system consists of mature crRNA that is base-paired to trans-activating crRNA (tracrRNA), forming a two-RNA structure that directs Cas9 to the locus of a desired double-stranded (ds) break in target DNA. In some embodiments base-paired tracrRNA:crRNA combination is engineered as a single RNA chimera to produce a et. al., Science. 2012; Mali, P., et. al., Nat Methods. 2013 October; 10(10): 1028-1034) and the sgRNA molecules are used sequence-specific target recognition, cleavage, and genome editing of the gene of interest. In one embodiment, the cleavage site is at a specific nucleotide, such as, but not limited to the 16, 17, or $18^{th}$ nucleotide of a 20 nucleotide target. In one non-limiting example, the cleavage site is at the $17^{th}$ nucleotide of a 20-nt target sequence (see FIG. 1 and FIG. 3). The cleavage can be a double stranded cleavage. The cleavage site can be in the coding region of any gene, or in a non-coding region, such as in a promoter, enhancer, intron, etc. In some embodiments, a loss of function is produced. In other embodiments, a gain of function is produced.

In some embodiments, the sgRNA molecule is selected so that the target genomic targets bear a protospacer adjacent motif (PAM). In some embodiments, DNA recognition by guide RNA and consequent cleavage by the endonuclease requires the presence of a protospacer adjacent motif (PAM) (e.g. 5'-NGG-3') in immediately after the target.

In some embodiments, cleavage occurs at a site about three base-pairs upstream from the PAM. In some embodiments, the Cas9 nuclease cleaves a double stranded nucleic acid sequence.

In some embodiments, the guide sequence is selected to reduce the degree of secondary structure within the sequence. Secondary structure may be determined by any suitable polynucleotide folding algorithm. Some programs are based on calculating the minimal Gibbs free energy. An example of one such algorithm is mFold (Zuker and Stiegler, Nucleic Acids Res. 9 (1981), 133-148). Another example folding algorithm is the online webserver RNAfold, which uses the centroid structure prediction algorithm (see e.g. A. R. Gruber et al., 2008, Cell 106(1): 23-24; and PA Can and GM Church, 2009, *Nature Biotechnology* 27(12): 1151-62). Guide sequences can be designed using the MIT CRISPR design tool found at crispr.mit.edu or the E-CRISP tool found at www.e-crisp.org/E-CRISP. Additional tools for designing tracrRNA and guide sequences are described in Naito Y et al., Bioinformatics. 2014 Nov. 20, and Ma et al. BioMed Research International, Volume 2013 (2013), Article ID 270805. The crRNA can be 18-48 nucleotides in length. The crRNA can be 18, 19, 20, 21, 22, 23, 24 or 25 nucleotides in length. In one example, the crRNA is 20 nucleotides in length. In additional embodiments, the tracrRNA is pre-optimized, and is 83 nucleotides in length, see SEQ ID NO: 3, see below:

```
                                           (SEQ ID NO: 3)
GTTTTAGAGCTAGAAATAGCAAGTTAAAATAAGGCTAGTCCGTTATCAAC
TTGAAAAAGTGGCACCGAGTCGGTGCTTTTTTT.
```

As noted above, the system disclosed herein can include a promoter, such as, but not limited to, a U6 or H1 promoter operably linked to one or more nucleotide sequences, such as the sgRNAs.

The U6 promoter can include the following nucleic acid sequence:

```
GAGGGCCTATTTCCCATGATTCCTTCATATTTGCATATACGATACAAGGC

TGTTAGAGAGATAATTGGAATTAATTTGACTGTAAACACAAAGATATTAG

TACAAAATACGTGACGTAGAAAGTAATAATTTCTTGGGTAGTTTGCAGTT

TTAAAATTATGTTTAAAATGGACTATCATATGCTTACCGTAACTTGAAA

GTATTTCGATTTCTTGGCTTTATATATCTTGTGGAAAGGACGAAACACC (SEQ ID NO: 4, see also GENBANK ® Accession No.

X07425.1, incorporate herein by reference).
```

Disclosed below is a U6 sgRNA sequence, wherein the tracrRNA is underlined. The tracer sequence includes seven thymidines for terminating RNA transcription. The small "g," "ga," and the second "g" border the SapIrev and SapI sites where the nucleic acid encoding the sgRNA is inserted.

```
                                                 (SEQ ID NO: 5)
GGCGCGCCGGATCCGAGGGCCTATTTCCCATGATTCCTTCATATTTGCAT

ATACGATACAAGGCTGTTAGAGAGATAATTGGAATTAATTTGACTGTAAA

CACAAAGATATTAGTACAAAATACGTGACGTAGAAAGTAATAATTTCTTG

GGTAGTTTGCAGTTTTAAAATTATGTTTAAAATGGACTATCATATGCTT

ACCGTAACTTGAAAGTATTTCGATTTCTTGGCTTTATATATCTTGTGGAA

AGGACGAAACACCgGAAGAGCgaGCTCTTCgGTTTTAGAGCTAGAAATAG

CAAGTTAAAATAAGGCTAGTCCGTTATCAACTTGAAAAAGTGGCACCGAG

TCGGTGCTTTTTTGGTACCGGCGCGCC
```

In some embodiments, more than one DNA break can be introduced by using more than one sgRNA. For example, two sgRNAs can be utilized, such that two breaks are achieved. When two or more sgRNAs are used to position two or more cleavage events, in a target nucleic acid, it is contemplated that in an embodiment the two or more cleavage events may be made by the same or different Cas9 proteins. For example, when two sgRNAs are used to position two double strand breaks, a single Cas9 nuclease may be used to create both double strand breaks.

In some embodiments, the disclosed methods include the use of one or more vectors comprising: a) doxycycline promoter operably linked to a nucleotide sequence encoding a Type II Cas9 nuclease, b) a U6 promoter operably linked to one or more nucleotide sequences encoding one or more CRISPR-Cas guide RNAs that hybridize with the gene of interest in a eukaryotic cell. Components (a) and (b) can be located on same or different vectors, whereby the one or more guide RNAs target the gene of interest in the eukaryotic cell and the Cas9 protein cleaves the gene of interest. Thus, the sequence of the gene of interest is modified in the target cell. Suitable vectors are disclosed above.

The disclosed methods can be used to target any gene of interest, including increasing or decreasing expression. Thus disclosed herein are methods for the knock-in or knock-out of any gene.

Some targets, to the extent that they are present in or conditions of the liver are metabolic disorders, are: Amyloid neuropathy (TTR, PALB); Amyloidosis (APOA1, APP, AAA, CVAP, AD1, GSN, FGA, LYZ, PALB); Cirrhosis (KRT18, KRT8, CIRH1A, NAIC, TEX292, KIAA1988); hepatic steatosis (SIRT1, EGFR, GH, SIRT6); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1, HNF4a, FOXA2, FOXA1, HNF1a, FXR, LXR, PPRa, FOXO1, PGCA, PXR, CAR, RXR, NTCP, OATP, ABCA1, CX32, ABCB11), Hepatic lipase deficiency (LIPC), Hepatoblastoma, cancer and carcinomas (CTNNB1, PDGFRL, PDGRL, PRLTS, AXIN1, AXIN, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63)); liver regeneration (GH, JAK2, STAT5, SHC, SOS, GRB2, RAS, RAF, MEK, ERK1/2, FAK, P130, CRKII, MEKK, JNK, P38, IRS1-3, PI3K, AKT, PLC, PKC, GHR, IGF-1, IGF-2, ALS, SOCS2, SHP1, EGFR, AR, P21, HB-EGF, EGF, TGFa, C-SRC, STAT1, STAT3, P110, P85, AKT, mTOR, GSK3B, IKK, NFKB, CREB, PLC, PKC, PIP2, IP3, DAG, C-MYC, ADAM17, PDGFa, PDGFRa, PDGFRb, C/EBPa, p27), metabolic deficincies (OTC, ALB, AFP, TDO, PEPCK, UGT1A1, A1AT, TAT, ADH1, CPS), Liver detoxification (CYP2C9, CYP2C19, CYP2D6, CYP3A4, CYP3A7, CYP7A1, CYP1A2, CYP2B6, CYP2C8); Cholangiocyte function (CFTR, SOX9, CK7, CK19, HNF6, HNF1b). Other preferred targets include any one or more of include one or more of: PCSK9; Hmgcr; SERPINA1; ApoB; and.or LDL. Of course, the disclosed methods are not limited to targeting metabolic disorders. These targets are provided only by way of example.

In specific non-limiting embodiments, the gene of interest is SIRT1, SIRT6, SLC5A5, or β-catenin.

EXAMPLES

The disclosed methods produce iPSC or differentiated cells that undergo CRISR/Cas9 mediated recombination at a high frequency. As disclosed in FIG. 10, the efficiency of the present methods, wherein a doxycycline promoter operably linked to Cas9 is introduced into somatic cells before induction of iPSC is 40-50%, as compared with 0.1-3% when the same constructs are introduced directly into iPSC.

Example 1

Generation of Tet-On-Cas9 Lentivirus

A—Cas9 Validation

Two Cas9 plasmids were purchased (Addgene), one inhibiting Cas9 (Cas9i), one activating Cas9 (Cas9a). Both Cas9 sequences were PCR amplified and cloned into a validation vector pVal by recombinational cloning. NIH-3T3 cells were transfected at a confluency of about 50% with the validation plasmids pVal and were incubated under standard cell culture condition for 48 h. Total RNA was then isolated and 1 µg was reverse transcribed using a mixture of random hexamer and oligo-dT primer. The expression of Cas9i and Cas9a was determined by quantification of the target cDNA expression levels relative to that found in cells transfected with the NT control vector using the vector-encoded marker transcript as internal reference gene.

B—Tet-On-Cas9 Vector Construction (FIG. 1)

The one vector lentivirus Tet-On system pcLVi(3G) (Sirion Biotech), containing a tetracycline responsive element sequence (pTRE-3G), a ubiquitin C promoter (Pubq-c) and a tetracycline transactivator protein (rtTA-3G) and a puromycin resistance gene (PuroR) was used. The construct is schematized in FIG. 1. To create an inducible Tet-On-Cas9i/RFP lentiviral vector, we linearized Cas9i fragment and RFP sequences and ligated them together in pcLVi(3G) vector, following the pTRE-3G sequence (Cas9i/RFP is referred as "target sequence" in FIG. 1). To create an inducible construct Tet-On-Cas9a/GFP vector, we linearized a Cas9a fragment and GFP sequences and ligated them together in pcLVi(3G) vector, following the pTRE-3G sequence (Cas9a/GFP is referred as "target sequence" in FIG. 1). The cloning success was verified by sequencing.

C—Production of High Titer Lentivirus Stock $1 \times 10^6$ HEK-293T cells were transfected with either the linearized pcLVi(3G)-Tet-On-Cas9i/RFP or pcLVi(3G)-Tet-On-Cas9a-FFP lentiviral vectors to generate a high titer lentivirus production. After transfection, the culture medium was harvested and the vector stock concentrated. The biological titration of both lentivirus was performed through Lenti X qRT-PCR Titration kit (Clontech). This assay measures the number of lentivirus DNA copies integrated in the target cell genome. Each lentivirus yields $>1 \times 10^8$ viral particles. Each stock was preserved at −80 C.

Example 2

Transduction of Human Fetal Fibroblasts with Tet-On-Cas9 Lentivirus

A—Fetal Human Fibroblasts Isolation and Culture

De-identified fetal tissues were obtained with written informed consent. Human fetal fibroblasts (hFF) were isolated from fetal livers obtained after the termination of pregnancy performed at 20-23 weeks of gestation. Primary hFF were isolated by digesting the tissue in EMEM (Lonza, Walkersville, MD), which contains 0.5 mg/ml of collagenase (Type XI, SigmaAldrich, Saint-Louis MO, Cat. #C7657), on a lab shaker for 40 minutes. Viability was assessed by trypan blue exclusion test and was routinely >85%. Fetal fibroblasts were plated at a density of $1.3 \times 10^5$ cells/cm2 on type I rat tail collagen coated 12 well plates (Corning, Corning, NY). Cells were cultured and passaged 2 times to get a 100% pure population of hFF, with a DMEM medium (Gibco, Life Technologies, Carlsbad, CA, USA) containing 1× penstrep, 10-7M of insulin (Sigma-Aldrich, Saint-Louis, MO), and 5% bovine serum albumin (Gibco, Life Technologies, Carlsbad, CA, USA).

Figure 3:
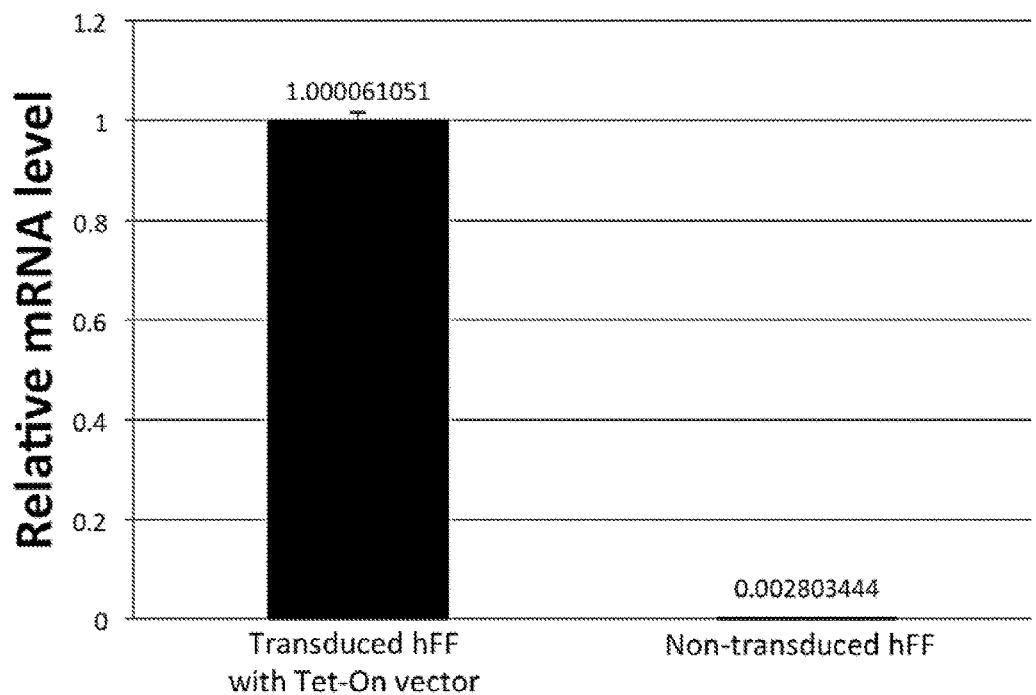
FIG. 3. Puromycin resistance gene expression in transduced and non-transduced hFF assessed by means of qRT-PCR.
Figure 4:
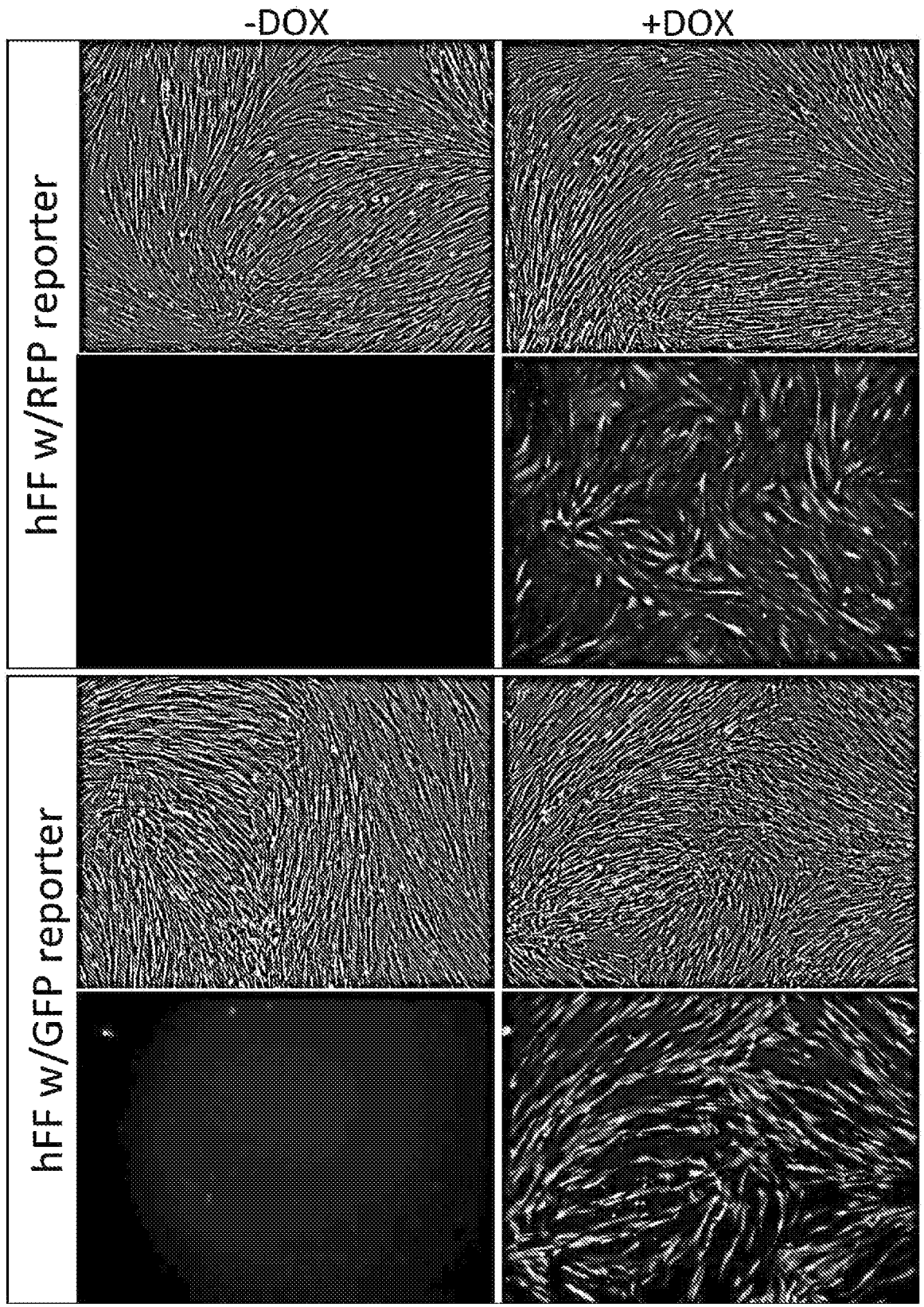
FIG. 4. Bright field and live florescence microscopy of hFF with fluorescent RFP and GFP markers 48 h after doxycycline induction.

B—Tet-On-Cas9 Lentiviral Transduction of Human Fetal Fibroblasts hFF were transduced with specific lentiviral particles (Tet-On-Cas9i/RFP and Tet-On-Cas9a/GFP) at an MOI of 15. The transduced cells were selected 72 h after transduction with 0.5 µg/mL of puromycin for 21 days to generate a stable pool of transduced cells. Non-transduced cells died within 7 days of puromycin selection (FIG. 2). After selection, total RNA was isolated from the treated hFF. 1 µg was reverse transcribed using a mixture of Random Hexamer and Oligo-dT primer. A qRT-PCR for the puromycin antibiotic selection cassette was performed (FIG. 3). The two cell pools generated (hFF-Tet-On-Cas9i/RFP and hFF-Tet-On-Cas9a/GFP) were tested for absence of lentiviral particles in culture medium of cell pools delivered with a detection of $1.0 \times 10^3$ genomic copies/ml (qRT-PCR)=$1.0 \times 10^{10}$ infection units (IU)/ml (by Flow Cytometry based assay). Quality control tests included viability, sterility (with CASO-Bouillion, Heipha) and mycoplasma testing (VENOR®GeM PCR-based mycoplasma test, Minerva Biolabs).

C—Validation of hFF-Tet-On-Cas9 Inducible System Efficiency

Figure 5:
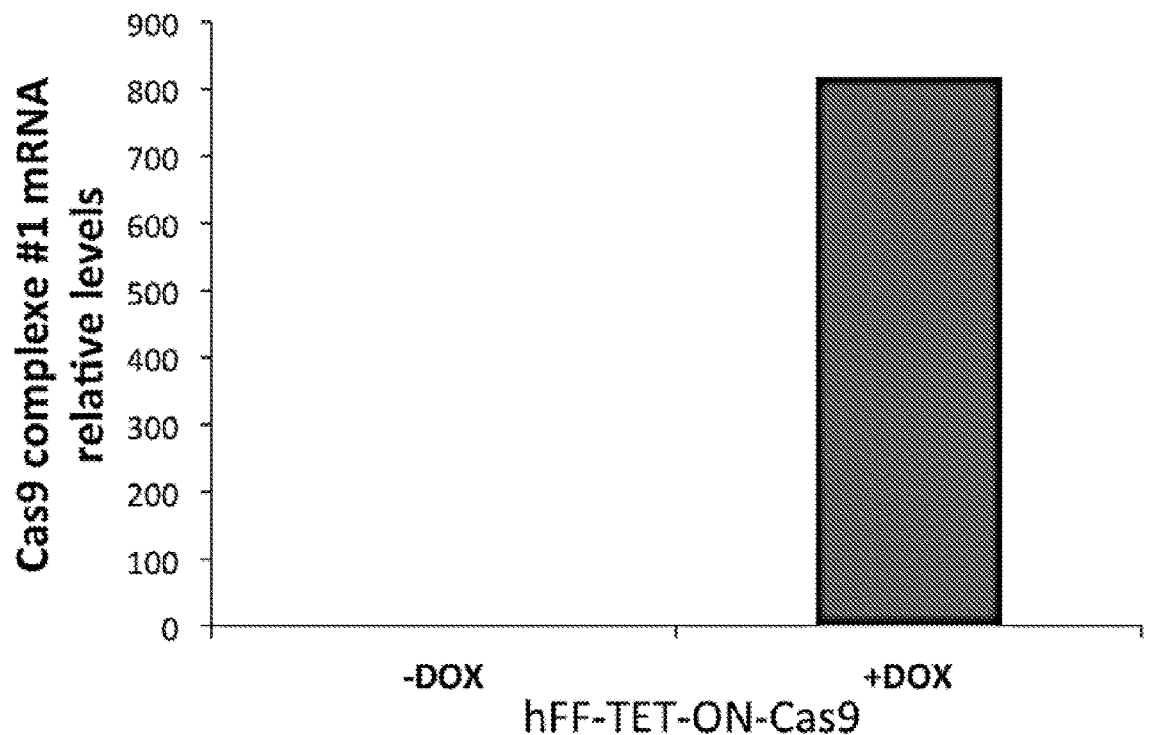
FIG. 5. Cas9 complex #1 and #2 in hFF-TET-ON-Cas9 with and without addition of doxycycline for 48 h assessed by means of RTqPCR.
Figure 5:
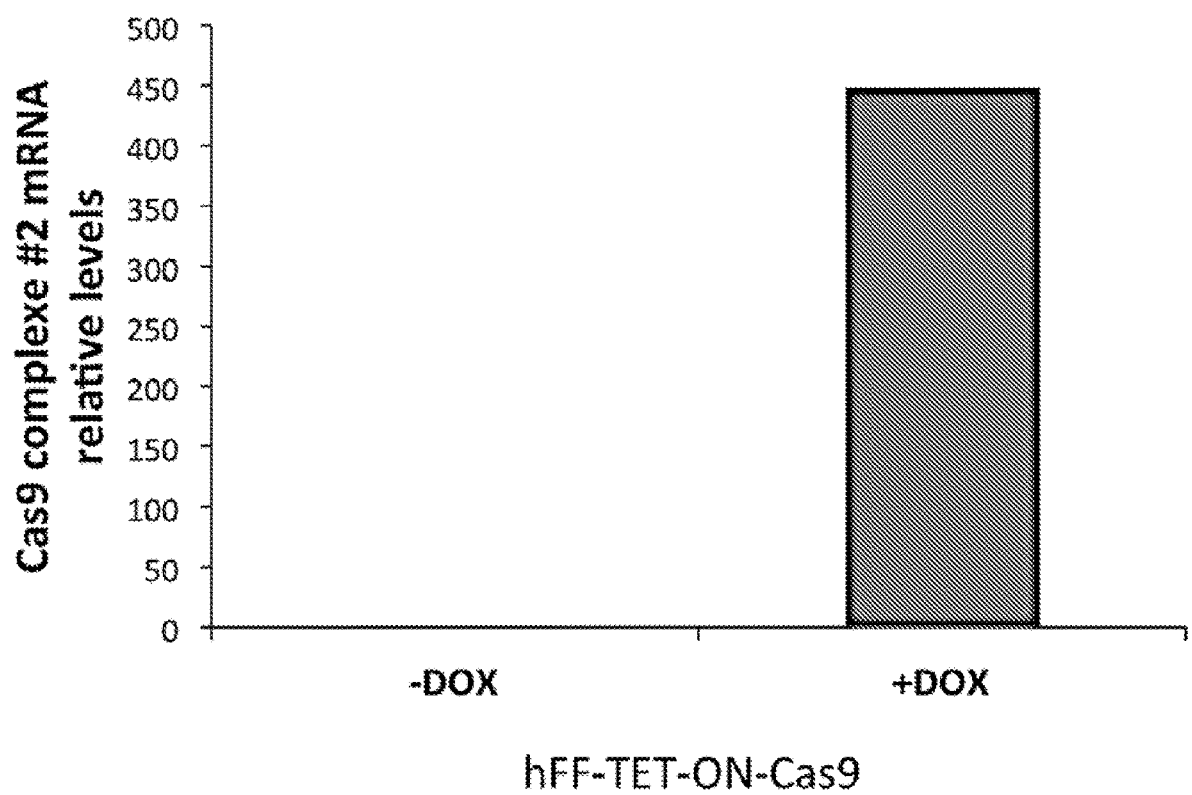

To test each cell lines for Cas9 efficiency, doxycycline was added to a final concentration of 0.5 µg/ml and cells were cultivated for 48 hours (h). The presence of fluorescent reporter proteins (RFP or GFP) was monitored by fluorescence microscopy (FIG. 3). Total RNA was isolated from each well and 1 µg was reverse transcribed using a mixture of Random Hexamer and Oligo-dT primer. The expression of each Cas9 was determined by quantification of the target cDNA expression levels relative non-induced cells and a reference gene (FIG. 5). The below results presented herein show reprogramming, screening and characterization of hiPS-TET-ON-TagRFP cells. The methods and results will be identical to reprogramming, screening and characterization of hiPS-TET-ON-Cas9-GFP or hiPS-TET-ON-Cas9-RFP systems.

Example 3

Generation of Human iPS Cells Carrying an Inducible Tet-On-TagRFP System

Figure 6:
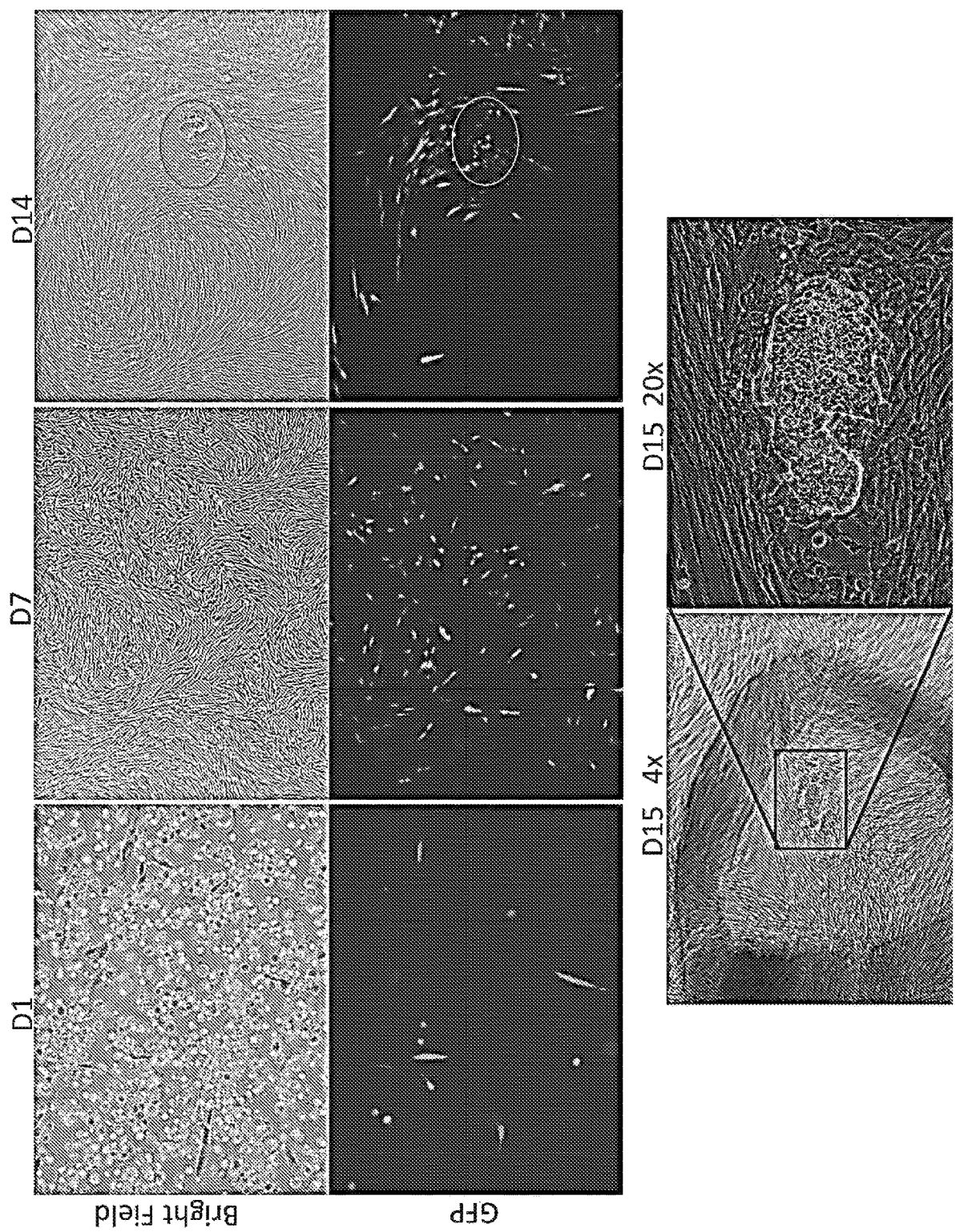
FIG. 6. Bright Field and live fluorescence microscopy of hFF-TET-ON-TagRFP reprogramming into hiPS-TET-ON-TagRFP. hFF transduced with GFP be followed up to 14 days after transduction. Clones started to appear at day 15.

A—hFF-Tet-On-TagRFP Reprogramming into Human iPS-Tet-On-TagRFP Cells hFF-TET-ON-TagRFP were reprogrammed into human iPS (hiPS) cells using episomal plasmids vectors (containing Oct3/4; Sox; Klf4; Lin; MycI and GFP) at 1 ug/mL with Lonza Nucleofactor kit (FIG. 6). The cells were culture under mTeSR medium. After 3 weeks, more than 30 hiPS clones were selected and were expanded separately for screening.

B—Screening for Positive hiPS-Tet-On-TagRFP Cells

Figure 7:
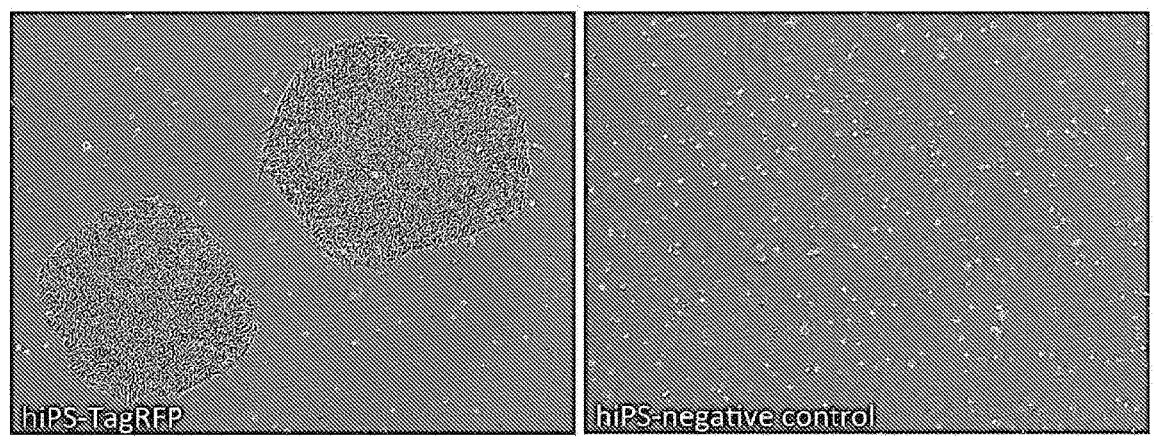
FIG. 7. Bright field microscopy hiPS-TET-ON-TagRFP and hiPS-negative control after 24 h of puromycin selection.
Figure 8:
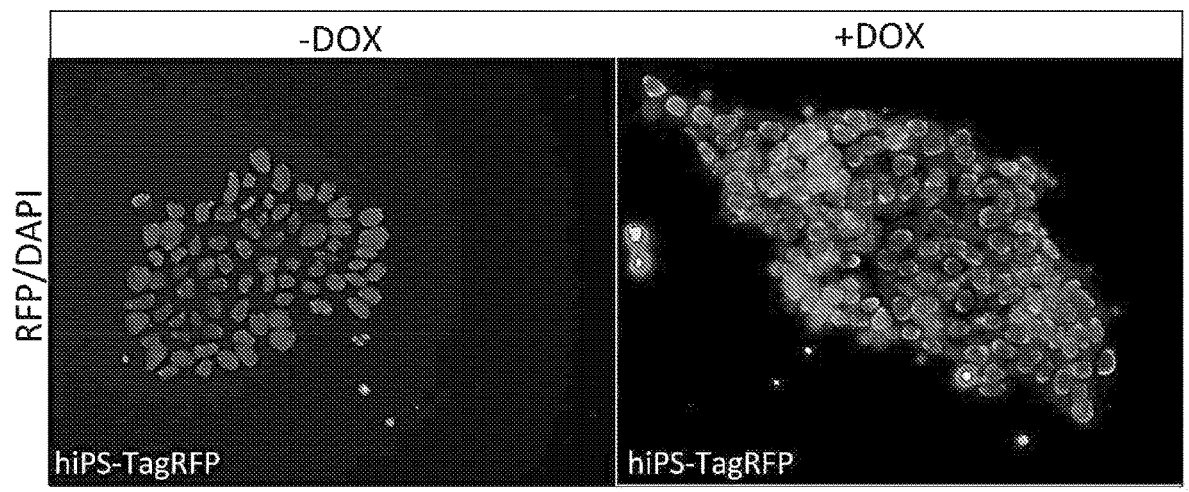
FIG. 8. Fluorescence microscopy of hiPS-TET-ON-TagRFP 48 h after doxycyclin exposure. Nuclei were counterstained with DAPI.

To screen for positive colonies, puromycin was added to the culture medium of each hiPS clone at a concentration of 0.125 µg/mL. hiPS negative control cells died in 24 h whereas hiPS-Tet-On-TagRFP positive cells remained alive without any deleterious effects. Puromycin was kept in the medium for 15 days to ensure a 100% pure population of cells. hiPS-negative controls cells died within the first 24 h after puromycin addition (FIG. 7). To test for inducible systems efficiency, doxycycline was added to a final concentration of 0.5 µg/ml and cells were cultivated for 48 h. The presence of RFP was monitored by fluorescence microscopy (FIG. 8).

Figures 9, 10:
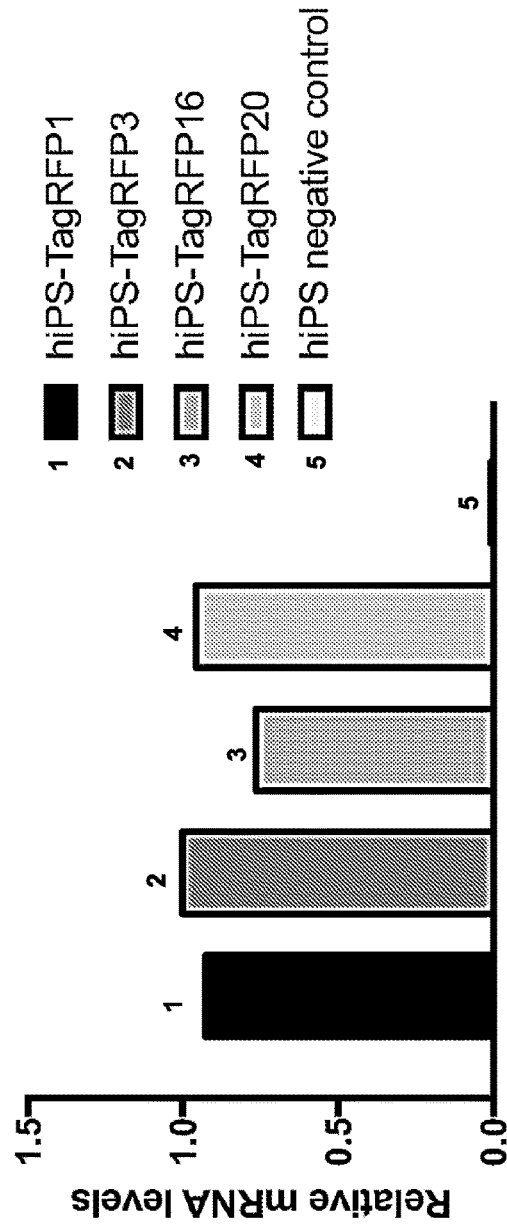
FIG. 9. Puromycin resistance gene expression in hiPS-TET-ON-TagRFP clones assessed by means of qRT-PCR.
FIG. 10. Summary table of hiPS-TET-ON-RFP generation and efficiency of inducible system.

Total RNA was isolated from each clone. 1 µg was reverse transcribed using a mixture of Random Hexamer and Oligo-dT primer. A qRT-PCR for the puromycin antibiotic selection cassette and for target genes was performed (FIG. 9). All hiPS clones carried the TET-ON-TagRFP systems and 39% exhibited high levels of RFP expression (FIG. 10).

C—Characterization of hiPS-Tet-On-TagRFP Cells

Figure 11B:
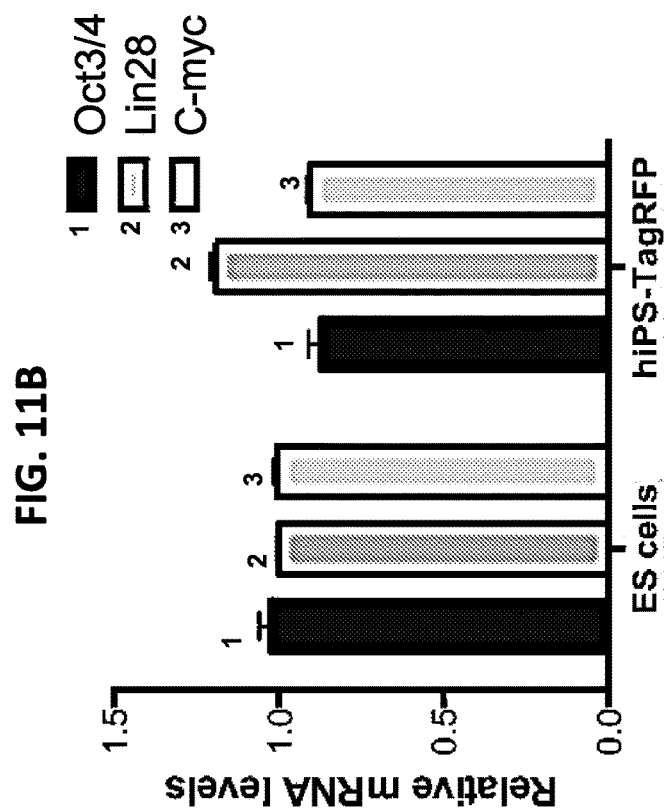
FIGS. 11A-11B. Characterization of hiPS-TET-ON-TagRFP cells. A) Immunofluorescence of Nanog, Oct3.4, TRA-1-60, SSEA4 in hiPS-TET-ON-TagRFP. Nuclei were counterstained with DAPI. B) Oct3/4, Lin28 and C-myc expression in ES and hiPS-TET-ON-TagRFP cells assessed by means of RTqPCR.
Figure 11A:
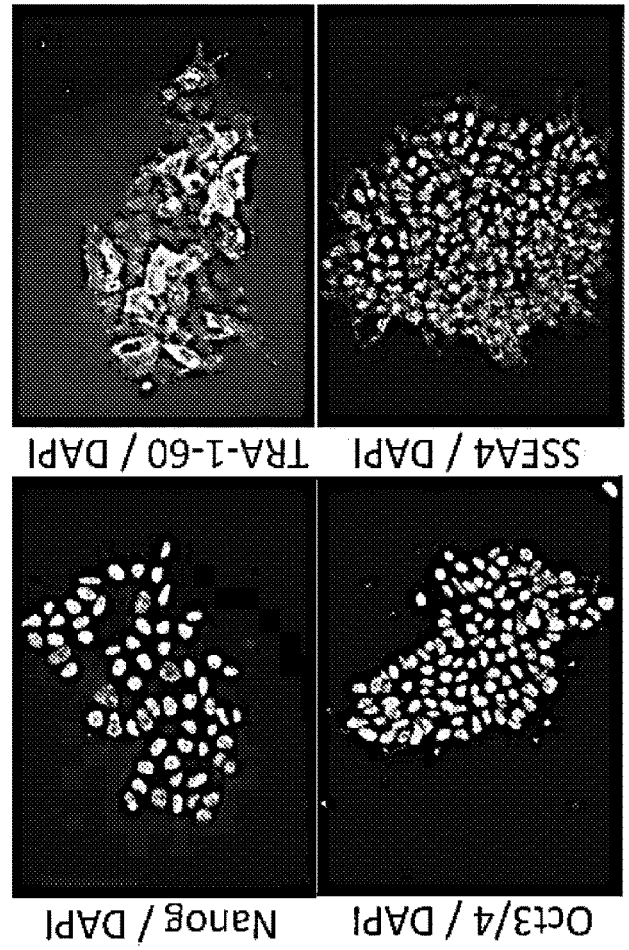

Immunofluorescent staining for pluripotency-associated proteins of Nanog, Oct3/4, TRA-1-60 and SSEA4 in hiPS-Tet-On-TagRFP cell line were performed (FIG. 11A). Expression of pluripotency-associated genes (Oct3/4; C-myc; Lin28) was also tested by qRT-PCR expression as was hiPS-TET-ON-TagRFP in cell lines (FIG. 11B).

Figure 12A:
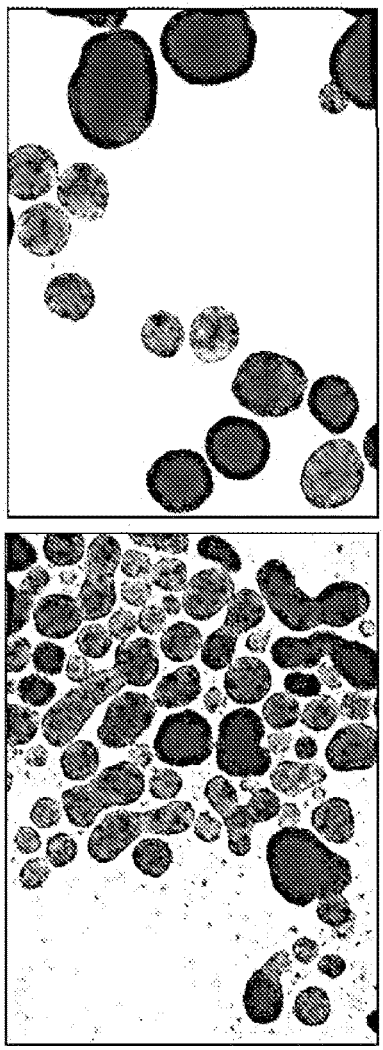
FIGS. 12A-12B. Generation of embryoid bodies with hiPS-TET-ON-TagRFP. A) Bright Field microscopy of hIPS-TET-ON-TagRFP 15 days after embryoid bodies formation. B) Immunofluorescence of the three germ layers GATA-4 and SOX17 for Endoderm, HAND1 and Brachyury for Mesoderm and Otx-2 and SOX1 for Ectoderm on hiPS-TET-ON-TagRFP. Nuclei were counterstained with DAPI.
Figure 12B:
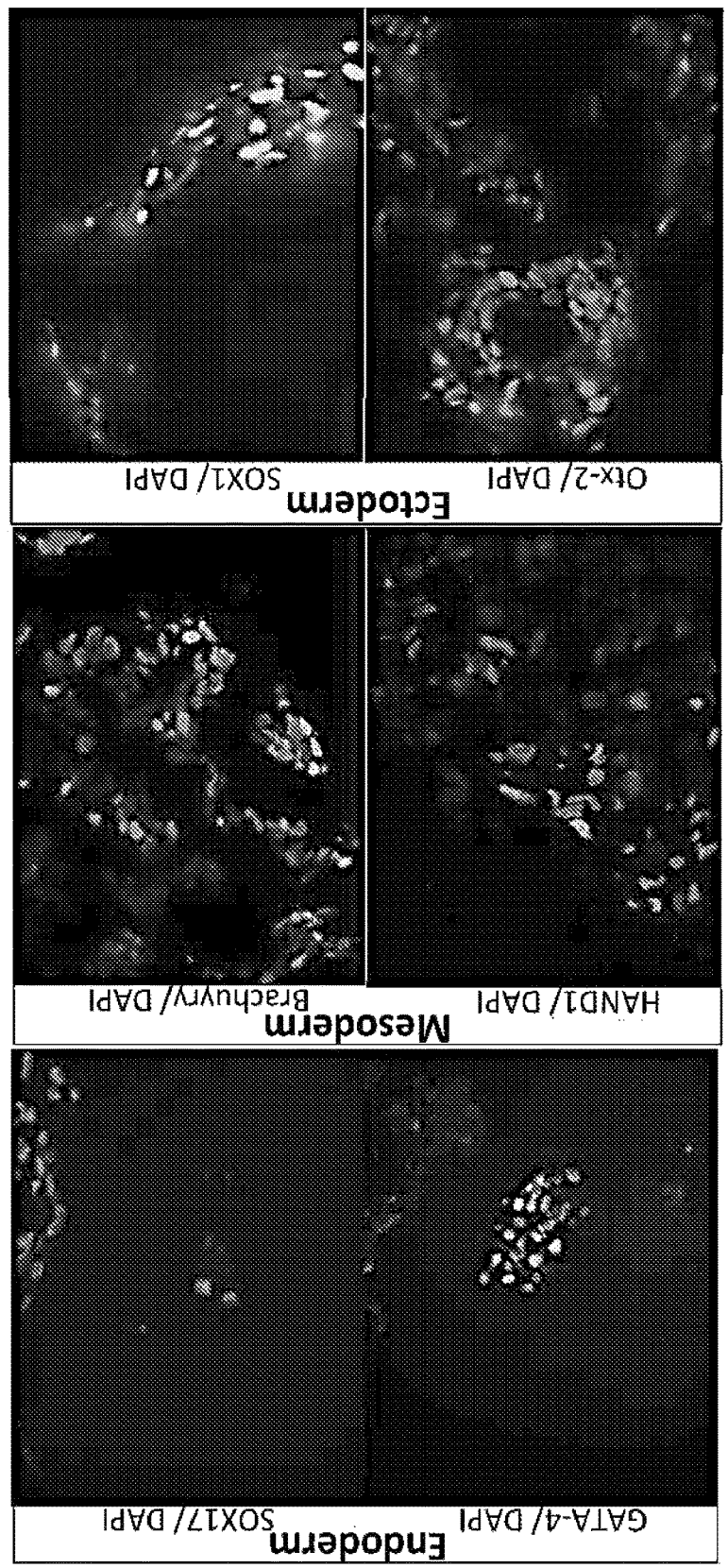

To form embryoid bodies, cells were washed once with PBS and detached with Dispase for 3 minutes at 37° C. Cells were resuspended in mTeSR medium with 20% Fetal Bovine Serum counted and plated at a concentration of 3 million cells per ml in 6 well low attachment plates for 20 days. Cells were fixed with 4% paraformaldehyde-PBS, blocked and permeabilized with BSA (1%)—Triton X-100 (0.1%)—Tween (0.1%). Germ layer differentiation was subsequently verified using the six fluorochrome-conjugated antibodies provided in the Human Three Germ Layer 3-Color Immunocytochemistry Kit (Catalog # SCO22): fluorochrome NL557-conjugated Otx2 (red) and NL493-conjugated SOX1 (green) for Ectoderm; NL557-conjugated Brachyury (red) and NL637-conjugated HAND1 (green) for Mesoderm; NL637-conjugated SOX17 (red) and NL493-conjugated GATA-4 (green) for Endoderm. All nuclei were counterstained with DAPI (blue) (FIGS. 12A, 12B).

Example 4

Figure 13:
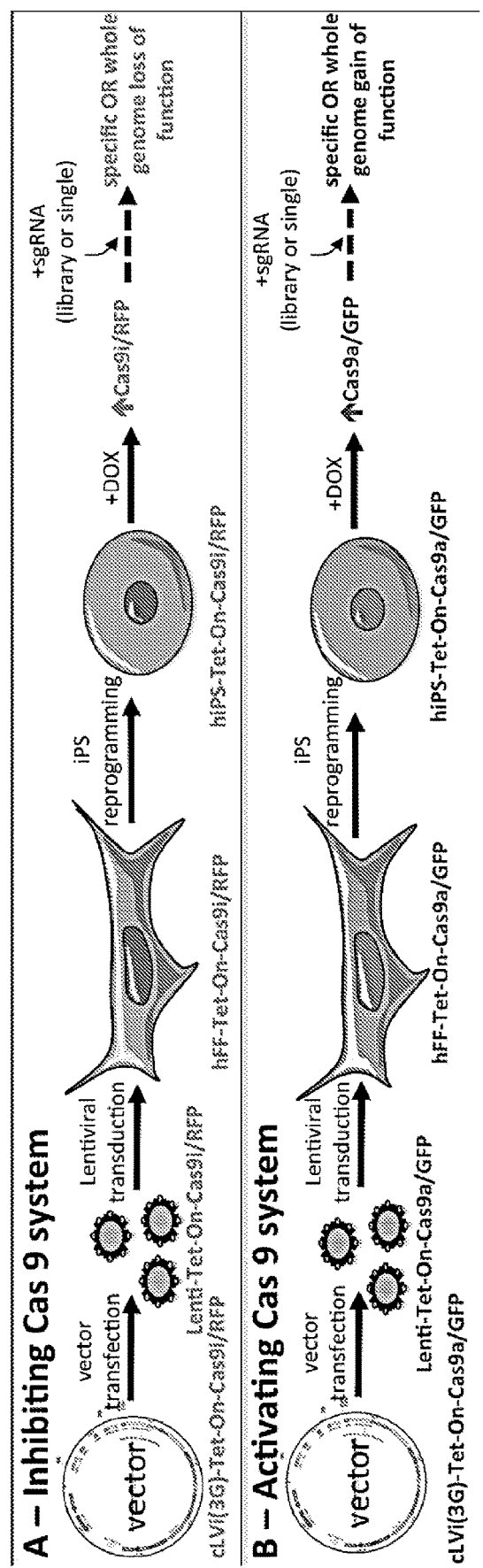
FIG. 13. Schematic of methods for generation of hiPS-Tet-On-Cas9 systems.

Functional Genome Editing and Screening with hiPS-Tet-On-Cas9 with Cas9/CRISPR Technology A schematic diagram of the technology is provided in FIG. 13.

A—Viral Production of sgRNA

A pooled plasmid library of single sgRNA (Addgene) will be transfected into HEK-293T cells with lentiviral packaging plasmids (Addgene). After transfection, the culture medium will be harvested and the vector stock concentrated.

B—hiPS-Tet-On-Cas9 Transduction with Lentivirus Containing sgRNA (FIG. 13)

Single sgRNA or pooled genome-wide human sgRNA library lentivirus can be used. Two days before transduction, Doxycycline is added to the medium of hiPS-Tet-On-Cas9i/RFP or hiPS-Tet-On-Cas9a/GFP cells. Both cell lines (before, during of after differentiation in any cell type) are transduced with lentivirus. The day after, positively transduced cells are selected, such as by adding an antibiotic selection.

C—In Vitro or In Vivo Assay of hiPS-Tet-On-Cas9 Genome Edition and Screening

Positively transduced cells are either cultured in vitro or transplanted in animal models. The functional assay evaluation depends on the screening test characteristic (ex: proliferation in vivo; tumor formation in vivo; drug resistance in vitro etc.).

1—In Vivo Screening for Regeneration:

Non-transduced or transduced iPS-derived cells are detached by trypsinisation and subsequently injected in the spleen of animals conditioned for liver regeneration, namely, hepatectomy, liver radiation, drug-induced liver DNA damage, etc. three months post-operation, animals are sacrificed and regenerative colonies are dissected by laser capture, DNA is extracted and analyzed through next generation sequencing.

2—In Vitro Screening for Drug Resistance Genes:

Positively transduced iPS-derived cells are selected by antibiotic selection and cultured into 96 well plates. The cells are screened by exposure to the drug of interest. DNA is isolated from drug-resistant populations in each screening compared to a non-treated control group and subjected to highthroughput sequencing analysis. In this experimental design gRNAs that confer survival will correspond to genes related to drug-resistance. This information can be used to identify mechanism for future target for disease (e.g. cancer, liver failure, regeneration, tissue preservation, etc.).

Example 5

Characterization of Cas9/CRISPR High Efficiency Activity of hiPS-Cas9/GFP

Methods:

A) hiPS-dCas9-SAM/GFP cells were cultivated for 48 h in presence or absence of doxycycline, expression of GFP was monitored and cells were harvested for RNA. B) hiPS-Cas9/GFP were cultured into a single cell medium culture (DEF-CS, Takara) and doxycycline was added for 48 h. Nucleofection was performed with plasmids carrying sgRNA for promoters of EGFR and HNF4 (sequences TGAGCTTGTTACTCGTGCCT (SEQ ID NO: 7) and GGGCGCGTTCACGCTGACCA (SEQ ID NO: 8), GenScript Cat# SC1823) or GFP as control.

hiPS-Cas9/GFP were culture for 48 hours in the presence or absence of doxycycline. The inducible expression of GFP was monitored in 100% of cells. RNA was harvested and the inducible expression of Cas9 system was confirmed (FIG. 14A).

As a proof of principle of CRISPR/Cas9 activity, a gain of function of two proteins normally expressed in differentiated hepatocytes, EGFR and HNF4 was tested in non-differentiated hiPS-Cas9/GFP. HNF4 is the most common hepatic nuclear factor found in the liver and a marker of specified hepatic cells. EGFR is a transmembrane protein and a receptor for extracellular protein ligands essential for hepatic proliferation. The expression of both proteins is required for efficient hepatic differentiation and proliferation. Non-differentiated hiPS-Cas9/GFP cells were culture into a single cell medium culture (DEF-CS, Takara) and doxycycline was added for 48 hours. hiPS-Cas9/GFP cells were nucleofected with two sgRNA coding for the promoters of EGFR or HNF4, purchased from GenScript SAM gRNA database, or GFP as control, at 4 ug/mL with P3 Primary Cell 4D-NUCLEOFECTOR® X Kit. 36 hours after nucleofection, total RNA was isolated from each well was reverse transcribed using a mixture of Random Hexamer and Oligo-dT primer. The expression of endogenous EGFR and HNF4 expression was determined by RTqPCR. The results showed a drastic increase of EGFR and HNF4 expression whenever the corresponding sgRNA was nucleofected in presence of doxycycline. This result confirms the activity of hiPS-Cas9/GFP as a tool for CRISPR/Cas9 high efficiency genetic engineering.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An in vitro method of producing a genetically modified human hepatocyte from induced pluripotent stem cells (iPSCs), comprising, (i) transfecting human somatic fibroblast cells with a lentiviral vector comprising an antibiotic selection cassette and a nucleic acid molecule comprising a) a doxycycline inducible promoter comprising a tetracycline responsive element operably linked to a nucleic acid encoding a Cas9, and b) a constitutive promoter operably linked to a tetracycline transactivator, wherein the tetracycline transactivator binds the tetracycline responsive element in the presence of doxycycline, to produce transfected human fibroblast cells;

(ii) culturing the transfected human fibroblast cells in the presence of the antibiotic for about three weeks to produce a population of stably transfected human fibroblast cells;

(iii) transfecting the stably transfected human fibroblast cells with at least four of: a nucleic acid molecule encoding Klf4, a nucleic acid encoding c-Myc, a nucleic acid encoding Oct4, a nucleic acid encoding Sox2, a nucleic acid encoding Nanog, a nucleic acid encoding Lin28, to produce the human iPSCs;

(iv) culturing the human iPSCs in the presence of the doxycycline to produce human iPSC expressing Cas9, wherein more than 50% of the human iPSCs express the Cas9 upon the exposure to the doxycycline;

(v) differentiating the human iPSCs expressing Cas9 into hepatocytes that express Cas9;

(vi) introducing a heterologous promoter operably linked to one or more nucleotide sequences encoding one or more CRISPR-Cas short guide RNAs (sgRNAs) that hybridize with a target gene into the hepatocytes of step (v); and (vii) culturing the hepatocytes of step (vi) in the presence of doxycycline, thereby producing a genetically modified human hepatocyte.

2. The method of claim 1, wherein the heterologous promoter is a U6 promoter.

3. The method of claim 1, wherein the guide RNAs mediate a knock-in of a gene.

4. The method of claim 1, wherein the guide RNAs mediate a knock-out of the target gene.

5. The method of claim 1, wherein the sgRNA gene targets a coding sequence for the target gene.

6. The method of claim 1, wherein the target gene is SIRT1, SIRT6, SLC5A5, or β-catenin.

7. The method of claim 1, wherein the Cas9 is SpCas9-HF1 or dCas9-VP64.

8. The method of claim 1, wherein the constitutive promoter is the ubiquitin C promoter.

9. The method of claim 1, wherein the target gene is SITR1.

10. The method of claim 1, wherein the target gene is UGT1A1 or CYP3A4.

11. The method of claim 1, comprising transfecting the stably transfected human fibroblast cells with the nucleic acid molecule encoding Oct3/4, the nucleic acid encoding Klf4, the nucleic acid encoding Sox2, and the nucleic acid encoding c-Myc and the nucleic acid encoding Lin28.

12. The method of claim 1, wherein the heterologous promoter is an ApoE promoter, an albumin promoter or an albumin promoter.

* * * * *

SEQUENCE LISTING

```
<160> NUMBER OF SEQ ID NOS: 10

<210> SEQ ID NO 1
<211> LENGTH: 334
<212> TYPE: DNA
<213> ORGANISM: Artificial Sequence
<220> FEATURE:
<223> OTHER INFORMATION: Tetracycline inducible promoter

<400> SEQUENCE: 1
atcgatacta gactcgagtt tactccctat cagtgataga gaacgtatga agagtttact    60
ccctatcagt gatagagaac gtatgcagac tttactccct atcagtgata gagaacgtat   120
aaggagttta ctccctatca gtgatagaga acgtatgacc agtttactcc ctatcagtga   180
tagagaacgt atctacagtt tactccctat cagtgataga gaacgtatat ccagtttact   240
ccctatcagt gatagagaac gtataagctt taggcgtgta cggtgggcgc ctataaaagc   300
agagctcgtt tagtgaaccg tcagatcgcc tgga                              334

<210> SEQ ID NO 2
<211> LENGTH: 1368
<212> TYPE: PRT
<213> ORGANISM: Streptococcus pyogenes

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
```

```
                145                 150                 155                 160
        Met Ile Lys Phe Arg Gly His Phe Leu Ile Glu Gly Asp Leu Asn Pro
                        165                 170                 175

Asp Asn Ser Asp Val Asp Lys Leu Phe Ile Gln Leu Val Gln Thr Tyr
                        180                 185                 190

Asn Gln Leu Phe Glu Glu Asn Pro Ile Asn Ala Ser Gly Val Asp Ala
                        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
        225                 230                 235                 240

Leu Ile Ala Leu Ser Leu Gly Leu Thr Pro Asn Phe Lys Ser Asn Phe
                        245                 250                 255

Asp Leu Ala Glu Asp Ala Lys Leu Gln Leu Ser Lys Asp Thr Tyr Asp
                        260                 265                 270

Asp Asp Leu Asp Asn Leu Leu Ala Gln Ile Gly Asp Gln Tyr Ala Asp
                        275                 280                 285

Leu Phe Leu Ala Ala Lys Asn Leu Ser Asp Ala Ile Leu Leu Ser Asp
                        290                 295                 300

Ile Leu Arg Val Asn Thr Glu Ile Thr Lys Ala Pro Leu Ser Ala Ser
        305                 310                 315                 320

Met Ile Lys Arg Tyr Asp Glu His His Gln Asp Leu Thr Leu Leu Lys
                        325                 330                 335

Ala Leu Val Arg Gln Gln Leu Pro Glu Lys Tyr Lys Glu Ile Phe Phe
                        340                 345                 350

Asp Gln Ser Lys Asn Gly Tyr Ala Gly Tyr Ile Asp Gly Gly Ala Ser
                        355                 360                 365

Gln Glu Glu Phe Tyr Lys Phe Ile Lys Pro Ile Leu Glu Lys Met Asp
                        370                 375                 380

Gly Thr Glu Glu Leu Leu Val Lys Leu Asn Arg Glu Asp Leu Leu Arg
        385                 390                 395                 400

Lys Gln Arg Thr Phe Asp Asn Gly Ser Ile Pro His Gln Ile His Leu
                        405                 410                 415

Gly Glu Leu His Ala Ile Leu Arg Arg Gln Glu Asp Phe Tyr Pro Phe
                        420                 425                 430

Leu Lys Asp Asn Arg Glu Lys Ile Glu Lys Ile Leu Thr Phe Arg Ile
                        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
        465                 470                 475                 480

Val Val Asp Lys Gly Ala Ser Ala Gln Ser Phe Ile Glu Arg Met Thr
                        485                 490                 495

Asn Phe Asp Lys Asn Leu Pro Asn Glu Lys Val Leu Pro Lys His Ser
                        500                 505                 510

Leu Leu Tyr Glu Tyr Phe Thr Val Tyr Asn Glu Leu Thr Lys Val Lys
                        515                 520                 525

Tyr Val Thr Glu Gly Met Arg Lys Pro Ala Phe Leu Ser Gly Glu Gln
                        530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                        565                 570                 575
```

-continued

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
                980                 985                 990
```

-continued

Val Gly Thr Ala Leu Ile Lys Lys Tyr Pro Lys Leu Glu Ser Glu Phe
995                  1000                 1005

Val Tyr Gly Asp Tyr Lys Val Tyr Asp Val Arg Lys Met Ile Ala
1010             1015                 1020

Lys Ser Glu Gln Glu Ile Gly Lys Ala Thr Ala Lys Tyr Phe Phe
1025             1030                 1035

Tyr Ser Asn Ile Met Asn Phe Phe Lys Thr Glu Ile Thr Leu Ala
1040             1045                 1050

Asn Gly Glu Ile Arg Lys Arg Pro Leu Ile Glu Thr Asn Gly Glu
1055             1060                 1065

Thr Gly Glu Ile Val Trp Asp Lys Gly Arg Asp Phe Ala Thr Val
1070             1075                 1080

Arg Lys Val Leu Ser Met Pro Gln Val Asn Ile Val Lys Lys Thr
1085             1090                 1095

Glu Val Gln Thr Gly Gly Phe Ser Lys Glu Ser Ile Leu Pro Lys
1100             1105                 1110

Arg Asn Ser Asp Lys Leu Ile Ala Arg Lys Lys Asp Trp Asp Pro
1115             1120                 1125

Lys Lys Tyr Gly Gly Phe Asp Ser Pro Thr Val Ala Tyr Ser Val
1130             1135                 1140

Leu Val Val Ala Lys Val Glu Lys Gly Lys Ser Lys Lys Leu Lys
1145             1150                 1155

Ser Val Lys Glu Leu Leu Gly Ile Thr Ile Met Glu Arg Ser Ser
1160             1165                 1170

Phe Glu Lys Asn Pro Ile Asp Phe Leu Glu Ala Lys Gly Tyr Lys
1175             1180                 1185

Glu Val Lys Lys Asp Leu Ile Ile Lys Leu Pro Lys Tyr Ser Leu
1190             1195                 1200

Phe Glu Leu Glu Asn Gly Arg Lys Arg Met Leu Ala Ser Ala Gly
1205             1210                 1215

Glu Leu Gln Lys Gly Asn Glu Leu Ala Leu Pro Ser Lys Tyr Val
1220             1225                 1230

Asn Phe Leu Tyr Leu Ala Ser His Tyr Glu Lys Leu Lys Gly Ser
1235             1240                 1245

Pro Glu Asp Asn Glu Gln Lys Gln Leu Phe Val Glu Gln His Lys
1250             1255                 1260

His Tyr Leu Asp Glu Ile Ile Glu Gln Ile Ser Glu Phe Ser Lys
1265             1270                 1275

Arg Val Ile Leu Ala Asp Ala Asn Leu Asp Lys Val Leu Ser Ala
1280             1285                 1290

Tyr Asn Lys His Arg Asp Lys Pro Ile Arg Glu Gln Ala Glu Asn
1295             1300                 1305

Ile Ile His Leu Phe Thr Leu Thr Asn Leu Gly Ala Pro Ala Ala
1310             1315                 1320

Phe Lys Tyr Phe Asp Thr Thr Ile Asp Arg Lys Arg Tyr Thr Ser
1325             1330                 1335

Thr Lys Glu Val Leu Asp Ala Thr Leu Ile His Gln Ser Ile Thr
1340             1345                 1350

Gly Leu Tyr Glu Thr Arg Ile Asp Leu Ser Gln Leu Gly Gly Asp
1355             1360                 1365

<210> SEQ ID NO 3
<211> LENGTH: 83
<212> TYPE: DNA

<213> ORGANISM: Artificial Sequence
<220> FEATURE:
<223> OTHER INFORMATION: tracrRNA

<400> SEQUENCE: 3

```
gttttagagc tagaaatagc aagttaaaat aaggctagtc cgttatcaac ttgaaaaagt    60
ggcaccgagt cggtgctttt ttt                                            83
```

<210> SEQ ID NO 4
<211> LENGTH: 249
<212> TYPE: DNA
<213> ORGANISM: Homo sapiens

<400> SEQUENCE: 4

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                           249
```

<210> SEQ ID NO 5
<211> LENGTH: 378
<212> TYPE: DNA
<213> ORGANISM: Artificial Sequence
<220> FEATURE:
<223> OTHER INFORMATION: U6 sgRNA

<400> SEQUENCE: 5

```
ggcgcgccgg atccgagggc ctatttccca tgattccttc atatttgcat atacgataca    60
aggctgttag agataatt ggaattaatt tgactgtaaa cacaaagata ttagtacaaa    120
atacgtgacg tagaaagtaa taatttcttg gtagtttgc agttttaaaa ttatgtttta   180
aaatggacta tcatatgctt accgtaactt gaaagtattt cgatttcttg gcttatata   240 tcttgtggaa aggacgaaac accggaagag cgagctcttc ggttttagag ctagaaatag   300
caagttaaaa taaggctagt ccgttatcaa cttgaaaaag tggcaccgag tcggtgcttt   360
ttttggtacc ggcgcgcc                                                 378
```

<210> SEQ ID NO 6
<211> LENGTH: 966
<212> TYPE: DNA
<213> ORGANISM: Homo sapiens

<400> SEQUENCE: 6

```
cgatacaagg ctgttagaga gataattaga attaatttga ctgtaaacac aaagatatta    60
gtacaaaata cgtgacgtag aaagtaataa tttcttgggt agtttgcagt tttaaaatta   120
tgttttaaaa tggactatca tatgcttacc gtaacttgaa agtatttcga tttcttggct   180
ttatatatct gtggaaaagg acgaaacacc ggagacggtt gtaaatgagc acacaaaata   240
cacatgctaa aatattatat tctatgacct ttataaaatc aaccaaaatc ttctttttaa   300
taactttagt atcaataatt agaatttta tgttcctttt tgcaaacttt taataaaaat   360
gagcaaaata aaaaaacgct agttttagta actcgcgttg ttttcttcac ctttaataat   420
agctactcca ccacttgttc ctaagcggtc agctcctgct tcaatcattt tttgagcatc   480
ttcaaatgtt ctaactccac cagctgcttt aactaaagca ttgtctttaa caactgactt   540
cattagttta acatcttcaa atgttgcacc tgattttgaa aatcctgttg atgttttaac   600
```

```
aaattctaat ccagcttcaa cagctatttc acaagctttc atgatttctt cttttgttaa    660
taaacaattt tccataatac atttaacaac atgtgatcca gctgctttt ttacagcttt     720 catgtcttct aaaactaatt cataatttt gtcttttaat gcaccaatat ttaataccat     780
atcaatttct gttgcaccat ctttaattgc ttcagaaact tcgaatgctt ttgtagctgt    840
tgtgcatgca cctagaggaa aacctacaac atttgttatt cctacatttg tgccttttaa    900
taattcttta caatagcttg ttcaatatga attaacacaa actgttgcaa aatcaaattc    960
aattgc                                                               966
```

```
<210> SEQ ID NO 7
<211> LENGTH: 20
<212> TYPE: DNA
<213> ORGANISM: Artificial Sequence
<220> FEATURE:
<223> OTHER INFORMATION: sgRNA for EGFR promoter

<400> SEQUENCE: 7
tgagcttgtt actcgtgcct                                                20

<210> SEQ ID NO 8
<211> LENGTH: 20
<212> TYPE: DNA
<213> ORGANISM: Artificial Sequence
<220> FEATURE:
<223> OTHER INFORMATION: sgRNA for HNF4 promoter

<400> SEQUENCE: 8
gggcgcgttc acgctgacca                                                20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gagggcctat ttcccatgat t                                              21

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gactatcata tgcttaccgt                                                20
```